(12) United States Patent
Bergmann et al.

(10) Patent No.: US 12,616,845 B2
(45) Date of Patent: May 5, 2026

(54) DEVICES AND RELATED METHODS FOR LIGHT-BASED MODULATION OF FOREIGN BODY RESPONSES IN LIVING TISSUE

(71) Applicant: KNOW Bio, LLC, Durham, NC (US)

(72) Inventors: Michael John Bergmann, Atlanta, GA (US); Mark Tapsak, Front Royal, VA (US); David T. Emerson, Durham, NC (US); F. Neal Hunter, Durham, NC (US); Andrew P. Gaudet de Lestard, Cary, NC (US)

(73) Assignee: KNOW Bio, LLC, Morrisville, NC (US)

( * ) Notice: Subject to any disclaimer, the term of this patent is extended or adjusted under 35 U.S.C. 154(b) by 307 days.

(21) Appl. No.: 17/330,569

(22) Filed: May 26, 2021

(65) Prior Publication Data

US 2021/0370088 A1     Dec. 2, 2021

Related U.S. Application Data

(60) Provisional application No. 63/031,970, filed on May 29, 2020, provisional application No. 63/032,022, filed on May 29, 2020.

(51) Int. Cl.
*A61N 5/06*      (2006.01)
*A61B 5/00*      (2006.01)
*A61B 5/145*     (2006.01)

(52) U.S. Cl.
CPC ......... *A61N 5/0601* (2013.01); *A61N 5/0616* (2013.01); *A61N 5/0624* (2013.01);
(Continued)

(58) Field of Classification Search
CPC ............... A61N 5/0601; A61N 5/0616; A61N 2005/0612; A61N 2005/0626;
(Continued)

(56) References Cited

U.S. PATENT DOCUMENTS 5,984,915 A * 11/1999 Loeb .................... A61B 18/203
606/15
6,584,335 B1     6/2003 Haar et al.
(Continued)

FOREIGN PATENT DOCUMENTS

EP        2965714 A1     1/2016
GB        2573011 A     10/2019
(Continued)

OTHER PUBLICATIONS

Ash et al. "Effect of wavelength and beam width on penetration in light-tissue interaction using computational methods" Lasers Med Sci (2017) 32:1909-1918 (Year: 2017).*
(Continued)

*Primary Examiner* — Lynsey C Eiseman
(74) *Attorney, Agent, or Firm* — Withrow & Terranova, P.L.L.C.

(57)          ABSTRACT

Modulation of foreign body responses in living tissue, and more particularly, devices and related methods for light-based modulation of foreign body responses in living tissue are disclosed. Light sources are disclosed that provide light with characteristics for modulation of foreign body responses that may be elicited by percutaneous and/or subcutaneous devices, including medical devices and other consumer electronic devices. Light delivery structures are disclosed that propagate light from the light sources to irradiate associated subcutaneous tissues. Modulation of foreign body responses may include inhibiting collagen and fibrous tissue generation, modulating inflammation and healing, and/or increasing nitric oxide production and/or release. By modulating foreign body responses associated with percutaneous and/or subcutaneous devices, performance characteristics and lifetimes of such devices may be improved.

26 Claims, 24 Drawing Sheets

(52) U.S. Cl.

CPC ........... *A61B 5/14532* (2013.01); *A61B 5/686* (2013.01); *A61N 2005/0612* (2013.01); *A61N 2005/0626* (2013.01); *A61N 2005/063* (2013.01); *A61N 2005/0632* (2013.01); *A61N 2005/0658* (2013.01); *A61N 2005/0663* (2013.01)

(58) Field of Classification Search

CPC .... A61N 2005/0632; A61N 2005/0658; A61N 5/0624; A61B 5/14532; A61B 5/1459; A61B 5/685; A61B 5/145; A61B 5/1495

See application file for complete search history.

(56) References Cited

U.S. PATENT DOCUMENTS

| | | | |
|---|---|---|---|
| 8,240,312 | B2 | 8/2012 | Feuerstein et al. |
| 8,435,273 | B2 | 5/2013 | Lum et al. |
| 8,838,228 | B2 | 9/2014 | Beisang, III et al. |
| 9,901,747 | B2 | 2/2018 | Gamelin et al. |
| 10,525,275 | B2 | 1/2020 | Stasko et al. |
| 10,639,498 | B2 | 5/2020 | Enwemeka et al. |
| 10,780,189 | B2 | 9/2020 | Randers-Pehrson et al. |
| 10,981,017 | B2 | 4/2021 | Enwemeka et al. |
| 11,266,855 | B2 | 3/2022 | Enwemeka et al. |
| 11,318,325 | B2 | 5/2022 | Rezaie et al. |
| 2002/0010500 | A1* | 1/2002 | Chen ..................... A61N 5/0601 607/89 |
| 2003/0004556 | A1* | 1/2003 | McDaniel .............. A61K 8/361 607/88 |
| 2003/0190120 | A1* | 10/2003 | Ziegenhagen ......... G02B 6/262 385/31 |
| 2005/0113658 | A1* | 5/2005 | Jacobson ............. A61B 5/4839 600/316 |
| 2008/0033519 | A1* | 2/2008 | Burwell ............... A61N 5/0601 607/122 |
| 2009/0257911 | A1* | 10/2009 | Thomas ................. B65D 77/26 422/186 |
| 2010/0152644 | A1* | 6/2010 | Pesach .............. A61M 5/14244 604/20 |
| 2010/0168806 | A1 | 7/2010 | Norlin-Weissenrieder et al. |
| 2010/0234793 | A1 | 9/2010 | Dacey, Jr. et al. |
| 2010/0249558 | A1* | 9/2010 | Yodfat ................. A61B 5/6833 600/345 |
| 2010/0292557 | A1* | 11/2010 | Pesach ................. A61B 5/1491 607/113 |
| 2010/0298764 | A1 | 11/2010 | Yodfat et al. |
| 2010/0303772 | A1* | 12/2010 | McMillan ......... A61M 5/14276 604/20 |
| 2012/0095532 | A1* | 4/2012 | Gertz ................... A61N 5/0603 607/88 |
| 2013/0006118 | A1* | 1/2013 | Pan ........................ H10K 71/00 257/E51.026 |
| 2016/0067519 | A1* | 3/2016 | Tranberg .............. A61N 5/0601 607/89 |
| 2019/0046812 | A1 | 2/2019 | Harlan et al. |
| 2019/0091389 | A1 | 3/2019 | Casas |
| 2020/0147406 | A1 | 5/2020 | Long et al. |
| 2021/0052760 | A1 | 2/2021 | Bouschbacher et al. |
| 2021/0196977 | A1 | 7/2021 | Zhang |
| 2021/0346500 | A1 | 11/2021 | Schikora |
| 2021/0402212 | A1 | 12/2021 | Schupp et al. |
| 2022/0088409 | A1 | 3/2022 | Dombrowksi et al. |

FOREIGN PATENT DOCUMENTS

| | | |
|---|---|---|
| JP | 2014529481 A | 11/2014 |
| WO | 2008022021 A2 | 2/2008 |
| WO | 2018232163 A1 | 12/2018 |

OTHER PUBLICATIONS

International Search Report and Written Opinion for International Patent Application No. PCT/US2021/034153, mailed Sep. 15, 2021, 17 pages.

Akiyama et al. "Macrophage inhibitory cytokine MIC-1 is upregulated by short-wavelength light in cultured normal human dermal fibroblasts" FEBS Letters, vol. 583, 2009, pp. 933-937.

Amar et al. "Power Approaches for Implantable Medical Devices" Sensors, vol. 15, 2015, pp. 28889-28914.

Author Unknown, "Clinical Evaluation Report: Dexcom Continuous Glucose Monitoring Systems" Dexcom, Inc., Revision 005, RPT-905497, 2018, 183 pages.

Author Unknown, "Luxeon CZ Color Line" Lumileds, DS198 Luxeon CZ Color Line Product Datasheet, 2020, 31 pages.

Author Unknown, "Visible Absorbance Spectroscopy of Glucose Oxidase Enzyme Kinetics in a Cuvette" Nicoya Lifesciences, 45 Water St S, Kitchener, ON, available at least as early as Apr. 28, 2021, 4 pages.

Avon et al. "Porcine Skin as an In-Vivo Model for Ageing of Human Bite Marks" The Journal of Forensic Odonto-Stomatology, vol. 23, No. 2, 2005, pp. 30-39.

Bashkatov et al. "Optical properties of human skin, subcutaneous and mucous tissues in the wavelength range from 400 to 2000nm" Journal of Physics D: Applied Physics, vol. 38, 2005, pp. 2543-2555.

Branski et al. "A porcine model of full-thickness burn, excision and skin autografting" Burns, vol. 34, No. 8, 2008, pp. 1119-1127.

Cappon et al. "Continuous Glucose Monitoring Sensors for Diabetes Management: A Review of Technologies and Applications" Diabetes & Metabolism Journal, vol. 43, 2019, pp. 383-397.

Darnell et al. "Evaluation of inactivation methods for severe acute respiratory syndrome coronavirus in noncellular blood products" Transfusion, vol. 46, No. 10, 2006, pp. 1770-1777.

Enwemeka et al. "Visible 405 nm SLD Light Photo-Destroys Methicillin-Resistant *Staphylococcus aureus* (MRSA) In Vitro" Lasers in Surgery and Medicine, vol. 40, 2008, pp. 734-737.

Goodman et al. "Cellular Chemotaxis Induced by Wear Particles from Joint Replacements" Biomaterials, vol. 31, No. 19, 2010, pp. 5045-5050.

Goodman et al. "The Effects of Bulk Versus Particulate Ultra-high-molecular-weight Polyethylene on Bone" The Journal of Arthroplasty, vol. 3, Supplement, 1988, pp. S41-S46.

Gibon et al. "The biological response to orthopedic implants for joint replacement. II: Polyethylene, ceramics, PMMA, and the foreign body reaction" Journal of Biomedical Materials Research Part B Applied Biomaterials, vol. 105, No. 6, 2016, pp. 1685-1691.

Gifford "Continuous Glucose Monitoring: 40 Years, What We've Learned and What's Next" ChemPhysChem, vol. 14, No. 10, 2013, pp. 2032-2044.

Gray et al. "Implantable biosensors and their contribution to the future of precision medicine" The Veterinary Journal, vol. 239, 2018, pp. 21-29.

Gupta et al. "Effect of red and near-infrared wavelengths on low-level laser (light) therapy-induced healing of partial-thickness dermal abrasion in mice" Lasers in Medical Science, vol. 29, 2014, pp. 257-265.

Kastellorizios et al. "Foreign Body Reaction to Subcutaneous Implants" Immune Responses to Biosurfaces, Advances in Experimental Medicine and Biology 865, Chapter 6, 2015, pp. 93-108.

Khanmohammadi et al. "Electrochemical biosensors for the detection of lung cancer biomarkers: A review" Talanta, vol. 206, 2019, pp. 120251.

Kvist et al. "Evaluation of Subcutaneously-implanted Glucose Sensors for Continuous Glucose Measurements in Hyperglycemic Pigs" in vivo, vol. 20, 2006, pp. 195-204.

Li et al. "The Histopathological Investigation of Red and Blue Light Emitting Diode on Treating Skin Wounds in Japanese Big-Ear White Rabbit" PLoS One, vol. 11, No. 6, 2016, 11 pages.

Lubart et al. "A Possible Mechanism for the Bactericidal Effect of Visible Light" Laser Therapy, vol. 20, No. 1, 2011, pp. 17-22.

Ma et al. "Effect of Low-Level Laser Therapy on Proliferation and Collagen Synthesis of Human Fibroblasts in Vitro" Journal of Wound Management and Research, vol. 14, No. 1, 2018, pp. 1-6.

(56) References Cited

OTHER PUBLICATIONS

Mamalis et al. "Light Emitting Diode-Generated Blue Light Modulates Fibrosis Characteristics: Fibroblast Proliferation, Migration Speed, and Reactive Oxygen Species Generation" Lasers in Surgery and Medicine, vol. 47, No. 2, 2015, pp. 210-215.

Mcclatchey et al. "Fibrotic Encapsulation Is the Dominant Source of Continuous Glucose Monitor Delays" Diabetes, vol. 68, 2019, pp. 1892-1901.

Mignon et al. "Differential Response of Human Dermal Fibroblast Subpopulations to Visible and Near-Infrared Light: Potential of Photobiomodulation for Addressing Cutaneous Conditions" Lasers in Surgery and Medicine, vol. 50, 2018, pp. 859-882.

Munap et al. "Wavelength and dose-dependent effects of photobiomodulation therapy on wound healing in rat model" Laser Physics, vol. 28, 2018, 5 pages.

Nakashima et al. "Induction of macrophage C—C chemokine expression by titanium alloy and bonecement particles" The Journal of Bone & Joint Surgery, vol. 81-B, No. 1, 1999, pp. 155-162.

Nauta et al. "Hypoxic Signaling During Tissue Repair and Regenerative Medicine" International Journal of Molecular Sciences, vol. 15, 2014, pp. 19791-19815.

Nichols et al. "Biocompatible Materials for Continuous Glucose Monitoring Devices" Chemical Reviews, vol. 113, No. 4, 2013, pp. 2528-2549.

Perdiz et al. "Distribution and Repair of Bipyrimidine Photoproducts in Solar UV-irradiated Mammalian Cells" The Journal of Biological Chemistry, vol. 275, No. 35, 2000, pp. 26732-26742.

Ravanat et al. "Direct and indirect effects of UV radiation on DNA and its components" Journal of Photochemistry and Photobiology B: Biology, vol. 63, 2001, pp. 88-102.

Rigla et al. "Human Subcutaneous Tissue Response to Glucose Sensors: Macrophages Accumulation Impact on Sensor Accuracy" Diabetes Technology & Therapeutics, vol. 20, No. 4, 2018, pp. 296-302.

Rochkind "Phototherapy in Peripheral Nerve Injury for Muscle Preservation and Nerve Regeneration" Photomedicine and Laser Surgery, vol. 27, No. 2, 2009, pp. 221-222.

Saura et al. "An Antiviral Mechanism of Nitric Oxide: Inhibition of a Viral Protease" Immunity, vol. 10, 1999, pp. 21-28.

Soto et al. "In Vivo Analytical Performance of Nitric Oxide-Releasing Glucose Biosensors" Analytical Chemistry, vol. 86, 2014, pp. 7141-7149.

Srivastava et al. "FreeStyle® Libre™ Flash Glucose Monitoring System: A Novel Diagnostic Technique for Monitoring Diabetes" International Journal of Contemporary Medicine Surgery and Radiology, vol. 3, No. 3, 2018, pp. C48-C52.

Summerfield et al. "The immunology of the porcine skin and its value as a model forhuman skin" Molecular Immunology, 2014, 8 pages.

Wang et al. "Red (660 nm) or near-infrared (810 nm) photobiomodulation stimulates, while blue (415 nm), green (540 nm) light inhibits proliferation in human adiposederived stem cells" Scientific Reports, vol. 7, No. 7781, 2017, 10 pages.

Wei et al. "Power sources and electrical recharging strategies for implantable medical devices" Frontiers in Energy, vol. 2, No. 1, 2008, pp. 1-13.

Willert et al. "Osteolysis in Alloarthroplasty of the Hip: The Role of Bone Cement Fragmentation" Clinical Orthopaedics and Related Research, vol. 258, 1990, pp. 108-121.

Examination Report for European Patent Application No. 21733316.0, mailed Apr. 11, 2025, 5 pages.

Notice of Reasons for Refusal for Japanese Patent Application No. 2022573539, mailed Apr. 14, 2025, 6 pages.

Final Decision of Rejection for Japanese Patent Application No. 2022-573539, mailed Sep. 18, 2025, 4 pages.

Decision to Grant for Japanese Patent Application No. 2022-573539, mailed Mar. 19, 2026, 5 pages.

* cited by examiner

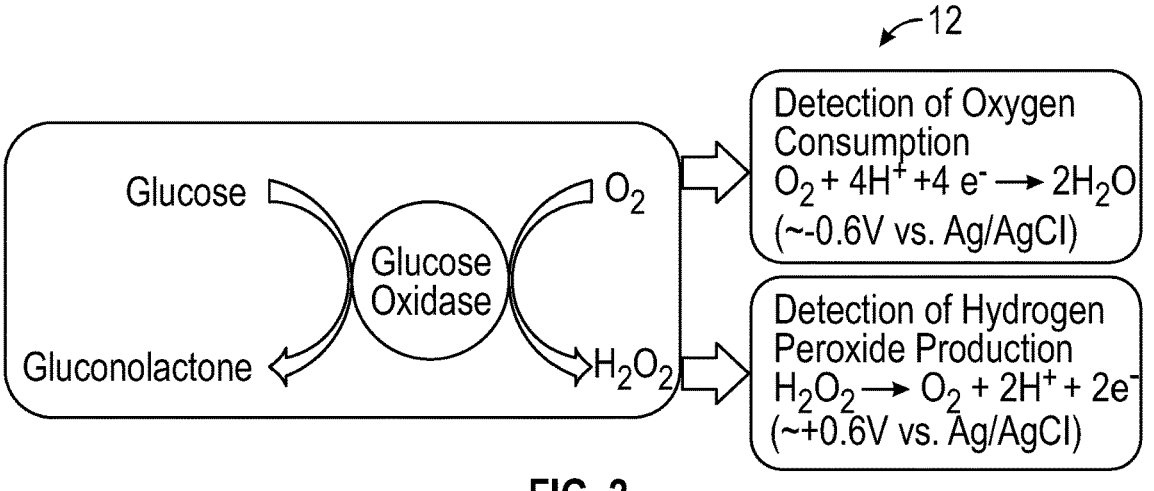
FIG. 2
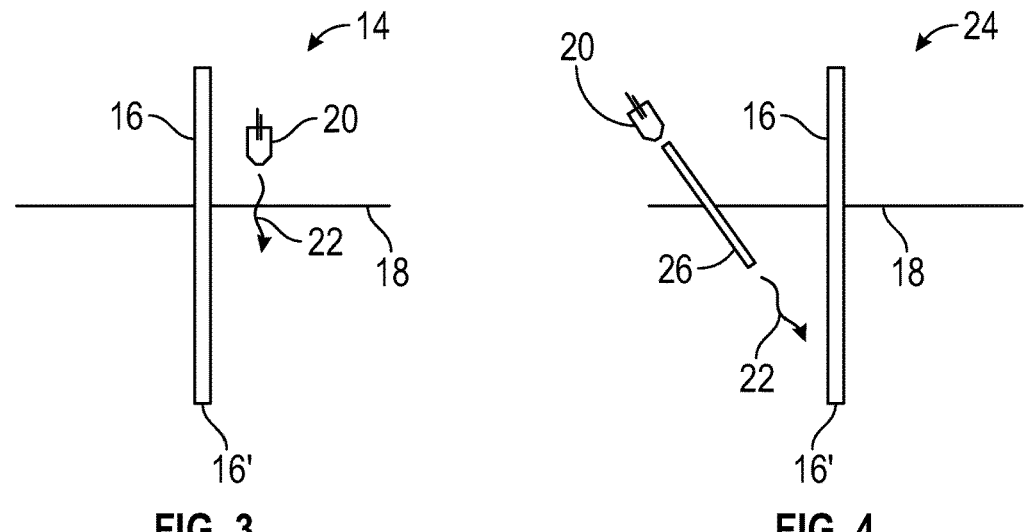
FIG. 3     FIG. 4
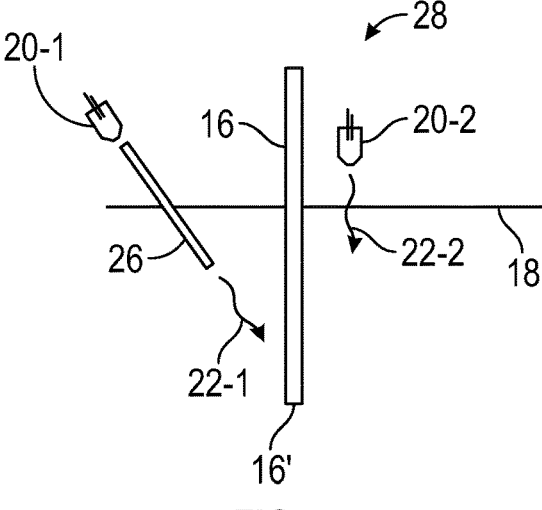
FIG. 5

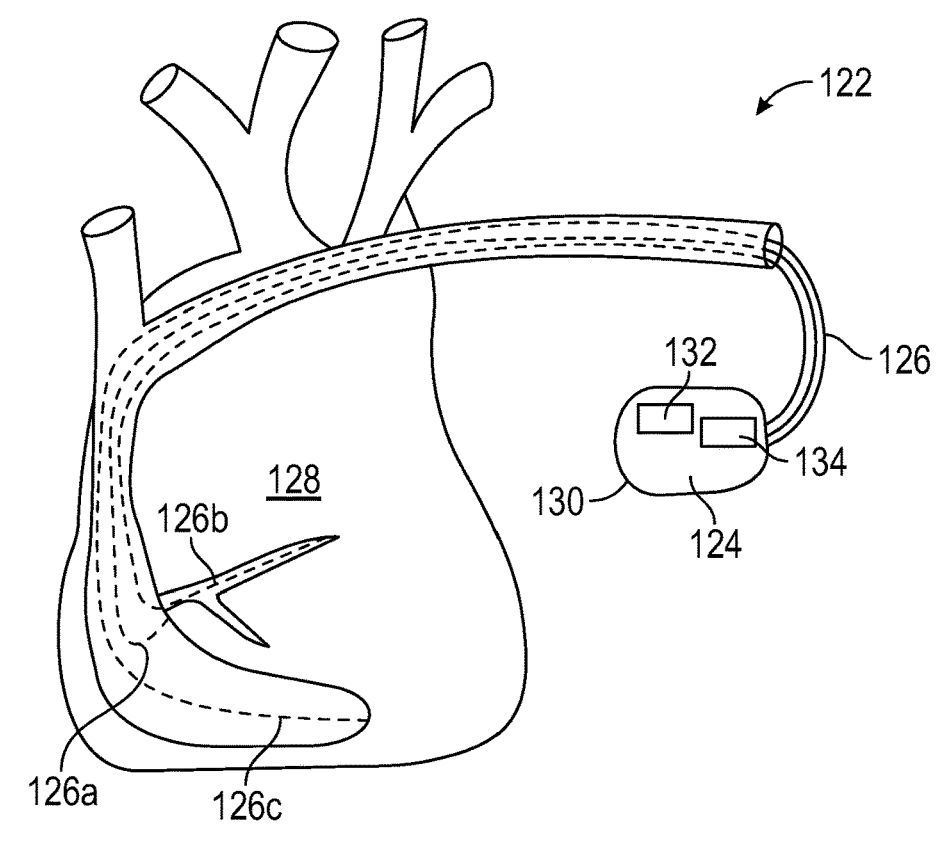
FIG. 20A
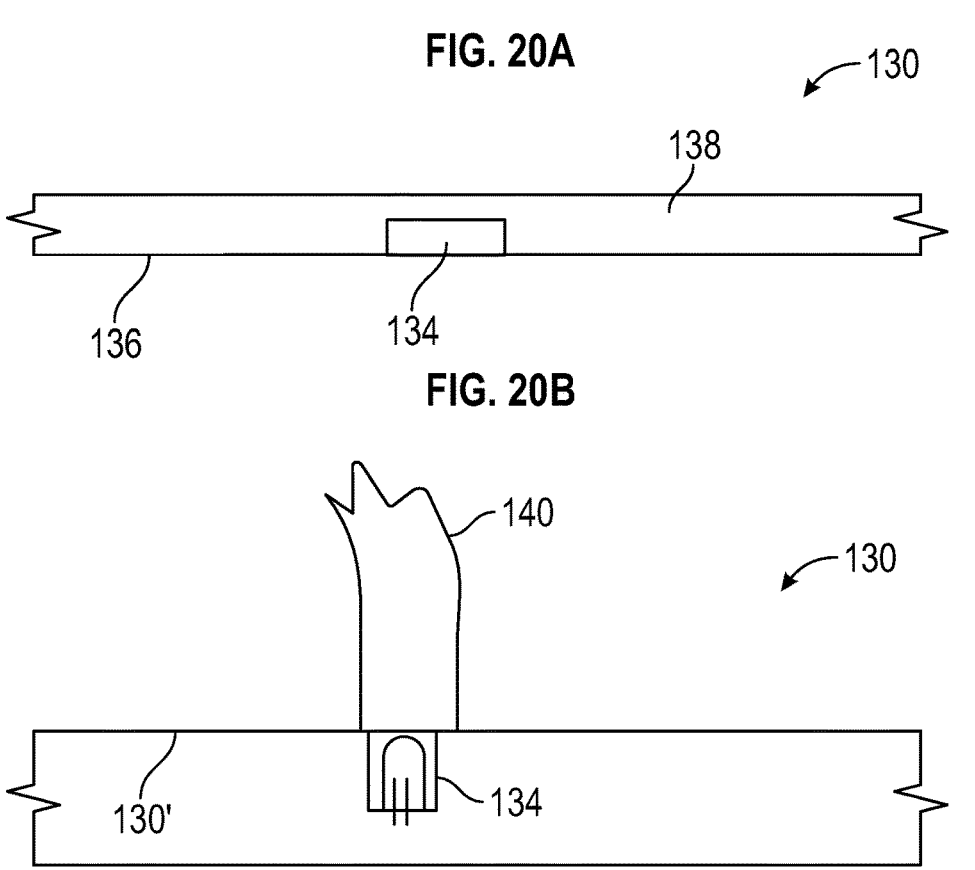
FIG. 20B
FIG. 20C

DEVICES AND RELATED METHODS FOR LIGHT-BASED MODULATION OF FOREIGN BODY RESPONSES IN LIVING TISSUE

RELATED APPLICATIONS

This application claims the benefit of provisional patent application Ser. No. 63/031,970, filed May 29, 2020, and provisional patent application Ser. No. 63/032,022, filed May 29, 2020, the disclosures of which are hereby incorporated herein by reference in their entireties.

FIELD OF THE DISCLOSURE

The disclosure relates generally to modulation of foreign body responses in living tissue, and more particularly, to devices and related methods for light-based modulation of foreign body responses in living tissue.

BACKGROUND

Foreign body response (FBR) generally initiates upon the insertion of a foreign object into subcutaneous tissue, starting with the creation of a wound and initiation of a body's innate wound healing cascade. Proteins can adhere to surfaces of the foreign body and associated protein adsorption can provide an interface that promotes adhesion of inflammatory cells during early stages of FBR. As FBR progresses, monocytes, macrophages, mast cells, and fibroblasts are signaled to the site of the foreign body to initiate clearance of the foreign body by releasing chemokines and cytokines. The concentrations and types of mediators released elicit further cell recruitment as the body may attempt phagocytosis to digest the foreign body. When digestion of the foreign body is unsuccessful, frustrated phagocytosis from activated macrophages can lead to the fusion of macrophages into foreign body giant cells (FBGCs) that attempt to further break down the foreign body. After a period of time, the FBR may progress to fibroblast infiltration and formation of a collagen matrix for encapsulation and sequestering of the foreign body from native tissue.

A wide variety of medical devices exist that are designed to be inserted percutaneously in order to extend through at least the epidermis and the dermis of a host, thereby having at least one region that resides in subcutaneous tissue. Additionally, other medical devices exist that are designed to be implanted subcutaneously so as to reside completely under the dermis of a host. Exemplary devices and applications include biometric sensors, catheters, pacemakers, prosthetics, breast implants, biomaterials, etc., and new devices and applications are constantly being developed. While a body's innate FBR may be useful in certain instances, the characteristic outcome of collagen encapsulation can be detrimental to the performance of some inserted or implanted medical devices. Continuous glucose monitors (CGMs) are an exemplary device where FBR can lead to adverse performance characteristics.

Diabetes mellitus is a worldwide epidemic characterized by chronic hyperglycemia that results from either a deficiency or tolerance of insulin. Blood glucose levels in diabetic patients can fluctuate significantly throughout the day, resulting in serious complications including heart attacks, strokes, high blood pressure, kidney failure, blindness and limb amputation. Portable glucose sensors give patients the ability to monitor blood glucose levels, manage insulin levels, and reduce the morbidity and mortality of diabetes mellitus. Traditional glucose monitoring techniques are primarily based on electrochemical amperometric glucose sensors. There are a number of approved biometric sensors for use as glucose monitors, with one example employing test strips with either glucose dehydrogenase (GDH) or glucose oxidase (GOx) immobilized on a screen-printed electrode. The analysis is based on obtaining a small blood sample, such as less than 1 microliter ($\mu$L), through a finger prick that is subsequently introduced into the test strip via capillary action. While these monitors have augmented the health outcomes for people with diabetes by improving blood glucose management, such monitoring only provides instantaneous blood glucose concentrations, and so such devices are unable to warn of hyperglycemic or hypoglycemic events in advance. Additionally, the sample collection (i.e., finger prick) method can be inconvenient, painful, and may result in poor patient compliance. Analytical methods that enable continuous monitoring of blood glucose have thus been sought.

CGMs have been developed that provide glucose levels at suitable time intervals, which can enable acquiring real-time information on trends (e.g., whether the glucose levels are increasing or decreasing), magnitude, duration, and frequency of glucose fluctuations during the day. CGM systems take glucose measurements at regular intervals, 24 hours a day, and translate the readings into dynamic data, generating glucose direction and rate of change. Having this context helps CGM users proactively manage glucose highs and lows, plus gives added insight into impacts that meals, exercise and illness may have on an individual's glucose levels. CGM can also contribute to better diabetes management by helping to reduce or minimize the guesswork that comes with making treatment decisions based solely on a number from a blood glucose meter reading.

Subcutaneous CGMs require surgery to insert them, and to later remove them, as they eventually need to be replaced. To overcome these limitations, percutaneous CGMs have been developed that include percutaneous needle-type microsensors that may monitor oxygen consumption or corresponding hydrogen peroxide production amperometrically as a measure of the glucose concentration.

While design, fabrication, and use criteria are important when using a CGM device, the innate FBR can profoundly impact bioanalytical and clinical utility. Long-term medical implants may be considered biocompatible or inert once the FBR resolves and the device is encapsulated by a collagen layer. However, for CGMs, the FBR can provide limitations to sensor accuracy and longevity. FBR effects on glucose sensor performance may be related to angiogenesis, cellular glucose consumption, capsule thickness, capsule diffusion coefficient, and capsule porosity. In some instances, FBR can result in a drop in local pH (e.g., to as low as 3.6) which can further disrupt biosensor performance, as the activity of GOx can be pH dependent. Decrease in mass transfer increases lag times and can potentially decrease the magnitude and differences when fluctuating between high and low glucose sensor signals. The decrease in mass transfer of important analytes, such as glucose and oxygen, potentially originates from collagen capsule thickness, blood vessel density, or other unanticipated factors associated with FBR. In this regard, accuracy and longevity of biosensors can be limited.

As the FBR sequence of events can directly impact the utility of medical devices such as CGMs, significant research has focused on improving biocompatibility of device elements as a strategy to improve associated sensor performance. These strategies range from chemical alteration at the tissue-sensor interface, changing physical properties of the device, and the release of biologically active molecules to influence the tissue reaction.

In the case of subcutaneously inserted or implanted devices, the FBR sequence can result in an initial inflammatory response or a gradual functionality loss over time. As the FBR sequence progresses, inflammatory cells can lead to formation of a collagen matrix that can attempt to sequester the device from native tissue. In the case where a subcutaneous implant moves within a full formed capsule, cells at the biointerface can be reinjured, thereby reinitiating the FBR sequence. This collagen encapsulation lacks the microvasculature of native tissue and can persist for the lifetime of the inserted or implanted device.

The art continues to seek improved devices and methods for mitigating FBR while being capable of overcoming challenges associated with conventional devices.

SUMMARY

The present disclosure relates generally to modulation of foreign body responses in living tissue, and more particularly, to devices and related methods for light-based modulation of foreign body responses in living tissue. Light sources are disclosed that provide light with characteristics for modulation of foreign body responses that may be elicited by percutaneous and/or subcutaneous devices, including medical devices and other consumer electronic devices. Light delivery structures are disclosed that propagate light from such light sources to irradiate associated subcutaneous tissues. Modulation of foreign body response may include inhibiting collagen and fibrous tissue generation, modulating inflammation and healing, and/or increasing nitric oxide production and/or release. By modulating foreign body responses associated with percutaneous and/or subcutaneous devices, performance characteristics and lifetimes of such devices may be improved.

In one aspect, a method of modulating a foreign body response comprises providing a foreign body within a region of subcutaneous tissue of a host; providing a light source capable of emitting one or more peak wavelengths of light; and irradiating one or more portions of the region of subcutaneous tissue with the light to modulate a foreign body response within the region of subcutaneous tissue. In certain embodiments, the light is irradiated to the one or more portions of the region of subcutaneous tissue at a tissue depth in a range from 1 millimeter (mm) to 15 mm. In certain embodiments, the light is irradiated to the one or more portions of the region of subcutaneous tissue at a tissue depth in a range from 4 mm to 15 mm. In certain embodiments, the one or more peak wavelengths of light comprises a first wavelength in a range from 315 nanometers (nm) to 600 nm, or in a range from 400 nm to 600 nm, or in a range from 600 to 1600 nm. In certain embodiments, the one or more peak wavelengths of light comprises a first wavelength in a range from 315 nm to 600 nm and a second wavelength that is different than the first wavelength, wherein the second wavelength is in a range from 600 nm to 1600 nm. In certain embodiments, the first wavelength is irradiated to the region of subcutaneous tissue during a first time interval and the second wavelength is irradiated to the region of subcutaneous tissue during a second time interval that is different than the first time interval. The first time interval may overlap with the second time interval, or the first time interval may be nonoverlapping with the second time interval. In certain embodiments, the first time interval is in a range from 3 to 30 days, and the second time interval is in a range from 0 days to 4 days. In certain embodiments, the second time interval is provided during hemostasis and inflammation stages of the foreign body response and the first time interval is provided during proliferation and remodeling stages of the foreign body response. The method may further comprise: providing a light source that is external to the host; providing a light delivery structure that is optically coupled with the light source; and inserting the light delivery structure through skin of the host to reach the one or more portions of the region of subcutaneous tissue. In certain embodiments, the light delivery structure comprises an optical waveguide. In certain embodiments, the light delivery structure comprises a fiber optic with a diameter in a range from 8 microns (μm) to 250 μm. In certain embodiments, the method may further comprise irradiating skin that is above the region of subcutaneous tissue with additional light.

In another aspect, a device comprises: a foreign body that is configured to be at least partially inserted within a region of subcutaneous tissue of a host; and a light source capable of emitting one or more peak wavelengths of light for irradiating one or more portions of the region of subcutaneous tissue to modulate a foreign body response within the region of subcutaneous tissue. In certain embodiments, the light source is provided outside the region of subcutaneous tissue for irradiating the light through a portion of the host's skin that is registered with the region of subcutaneous tissue. In certain embodiments, the device further comprises a light delivery structure that is optically coupled with the light source, wherein at least a portion of the light delivery structure is capable of residing within the region of subcutaneous tissue to irradiate one or more portions of the region of subcutaneous tissue. In certain embodiments, the device further comprises an additional light source that is provided for irradiating light through a portion of the host's skin that is registered with the region of subcutaneous tissue. In certain embodiments, the one or more peak wavelengths of light comprises a first wavelength in a range from 315 nm to 600 nm, or in a range from 400 nm to 600 nm, or in a range from 600 nm to 1600 nm. In certain embodiments, the one or more peak wavelengths of light comprises a first wavelength in a range from 315 nm to 600 nm and a second wavelength that is different than the first wavelength, wherein the second wavelength is in a range from 600 nm to 1600 nm. In certain embodiments, the device comprises a continuous glucose monitor and the foreign body comprises a sensor probe of the continuous glucose monitor. In further embodiments, the device comprises a light delivery structure that is optically coupled with the light source, wherein at least a portion of the light delivery structure is capable of residing within the region of subcutaneous tissue to irradiate one or more portions of the region of subcutaneous tissue.

In another aspect, a device comprises: a foreign body that is configured to be at least partially inserted within a region of subcutaneous tissue of a host; a light source capable of emitting one or more peak wavelengths of light; and a light delivery structure that is optically coupled with the light source, wherein at least a portion of the light delivery structure is capable of residing within the region of subcutaneous tissue to irradiate one or more portions of the region of subcutaneous tissue. In certain embodiments, the device is a continuous glucose monitor and the foreign body comprises a sensor probe of the continuous glucose monitor. In certain embodiments, the light delivery structure is arranged to surround one or more portions of the sensor probe. In certain embodiments, the light delivery structure is arranged in a parallel manner with the sensor probe. In certain embodiments, the light delivery structure is arranged in a nonparallel manner with the sensor probe. In certain embodiments, at least a portion of the light delivery structure is arranged within 0.5 mm of an active sensing region of the sensor probe. In certain embodiments, the one or more peak wavelengths of light comprises a first wavelength in a range from 315 nm to 600 nm, or in a range from 400 nm to 600 nm, or in a range from 600 nm to 1600 nm. In certain embodiments, the one or more peak wavelengths of light comprises a first wavelength in a range from 315 nm to 600 nm and a second wavelength that is different than the first wavelength, wherein the second wavelength is in a range from 600 nm to 1600 nm. In certain embodiments, the device is one of a pacemaker, an implantable cardioverter defibrillator, an implantable cardiac monitor, a cochlear implant, a joint replacement implant, a cosmetic implant, a drug delivery device, or an intrauterine device. In certain embodiments, the device may further comprise a power source that is configured to provide power to the light source and a control module that is configured to control dosing parameters of the light source. In certain embodiments, the power source comprises at least one of a battery and a rechargeable battery. In certain embodiments, the power source comprises an inductively coupled power supply. In certain embodiments, the control module comprises a microprocessor that actively controls the dosing parameters of the light source. In other embodiments, the control module may comprise a microcontroller. In certain embodiments, the dosing parameters of the light source are determined by external electronics. In certain embodiments, the power source is also configured to provide power to operate one or more functions of the foreign body. In certain embodiments, the power source and the control module are arranged externally to the region of subcutaneous tissue.

In another aspect, a continuous glucose monitor comprises: a sensor probe that is configured to monitor glucose concentrations in a host; a sensor holder that mechanically supports the sensor probe for percutaneous insertion in the host; a light source capable of emitting one or more peak wavelengths of light; and a light delivery structure that is optically coupled with the light source, wherein the light delivery structure is configured for percutaneous insertion in the host. In certain embodiments, the light delivery structure comprises an optical waveguide. In certain embodiments, the light delivery structure comprises a fiber optic with a diameter in a range from 8 μm to 250 μm. In certain embodiments, the light delivery structure is arranged in a parallel manner with the sensor probe. In certain embodiments, the light delivery structure is arranged in a nonparallel manner with the sensor probe. In certain embodiments, the light delivery structure is mechanically supported by the sensor holder. In certain embodiments, the light delivery structure comprises a length that is shorter than a length of the sensor probe. In certain embodiments, at least a portion of the light delivery structure is arranged within 0.5 mm of an active sensing region of the sensor probe. In certain embodiments, the light delivery structure is mechanically supported by a separate structure that is arranged between the sensor holder and the host. In certain embodiments, the light delivery structure is mechanically supported by a separate structure that is arranged along a lateral perimeter of the sensor holder. In certain embodiments, the one or more peak wavelengths of light comprises a first wavelength in a range from 315 nm to 600 nm, or in a range from 400 nm to 600 nm, or in a range from 600 nm to 1600 nm. In certain embodiments, the one or more peak wavelengths of light comprises a first wavelength in a range from 315 nm to 600 nm and a second wavelength that is different than the first wavelength, wherein the second wavelength is in a range from 600 nm to 1600 nm.

In another aspect, any of the foregoing aspects individually or together, and/or various separate aspects and features as described herein, may be combined for additional advantage. Any of the various features and elements as disclosed herein may be combined with one or more other disclosed features and elements unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

FIG. 2 is a schematic illustration of chemical reactions used to measure glucose concentrations, based on enzyme-modified electrodes and electrochemical detection.

FIG. 3 is an illustration showing a portion of a device that includes a foreign body for percutaneous placement through skin of a host and further includes FBR-modulating capabilities according to principles of the present disclosure.

FIG. 4 is an illustration showing a portion of a device that includes delivery of light at increased depths beneath the skin to provide FBR-modulating capabilities according to principles of the present disclosure.

FIG. 5 is an illustration of a portion of a device that includes a combination of FBR-modulating capabilities as described for the devices of FIG. 3 and FIG. 4.

FIG. 20A schematically depicts a pacemaker that may include light-based FBR modulating capabilities according to the present disclosure.

FIG. 20B is a schematic view of a portion of the housing of FIG. 20A, illustrating an arrangement of the light source for providing FBR-modulating capabilities.

FIG. 20C is a schematic view of a portion of a surface of the housing of FIG. 20A, illustrating another arrangement of the light source.

Figure 21:
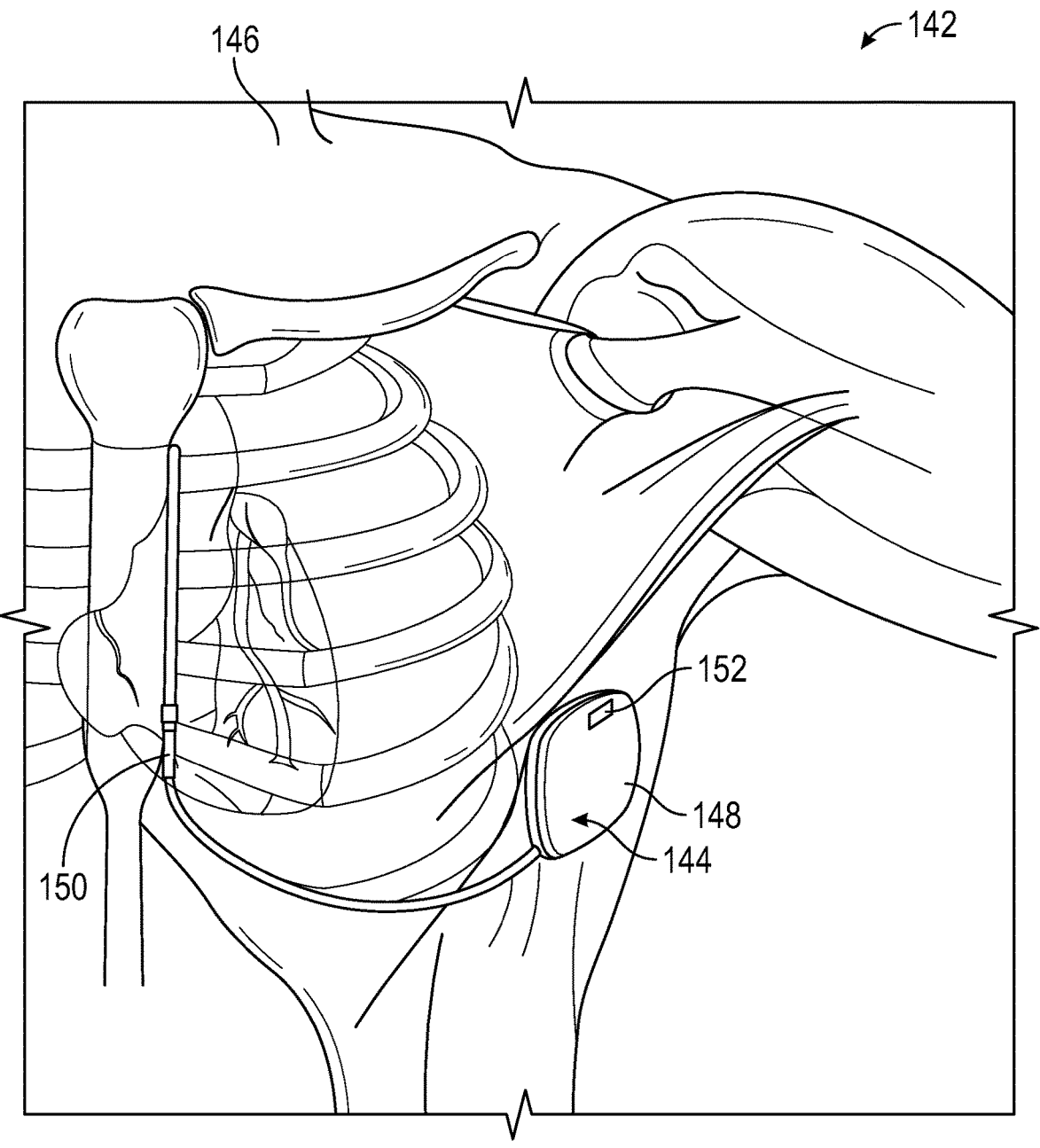

FIG. 21 is a schematic view of an implantable cardioverter defibrillator (ICD) implanted in a patient, where the ICD includes FBR-modulating capabilities according to the present disclosure.

Figure 22:
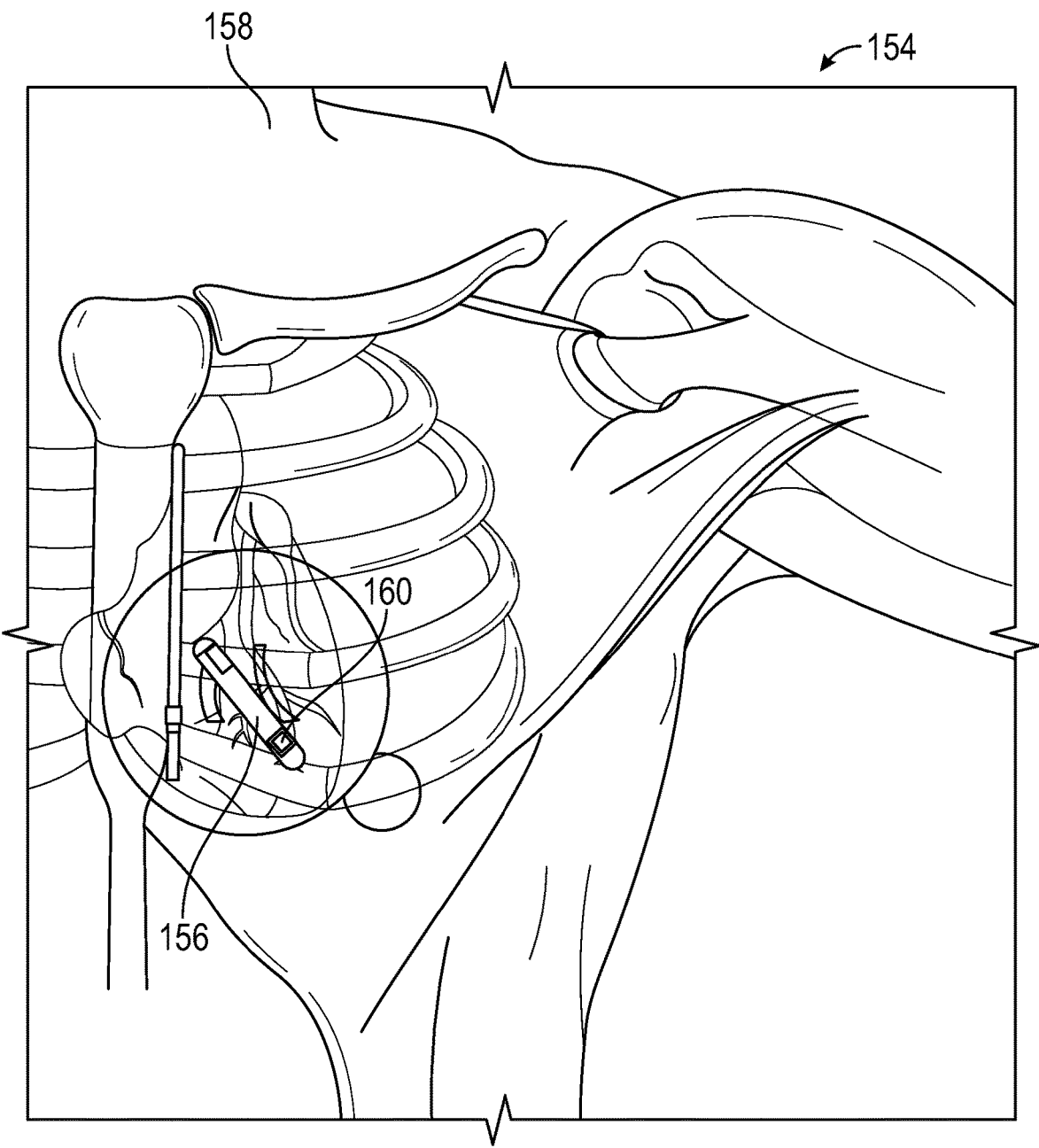

FIG. 22 is a schematic view of an implantable cardiac monitor (ICM) implanted in a patient, where the ICM includes FBR-modulating capabilities according to the present disclosure.

Figure 23:
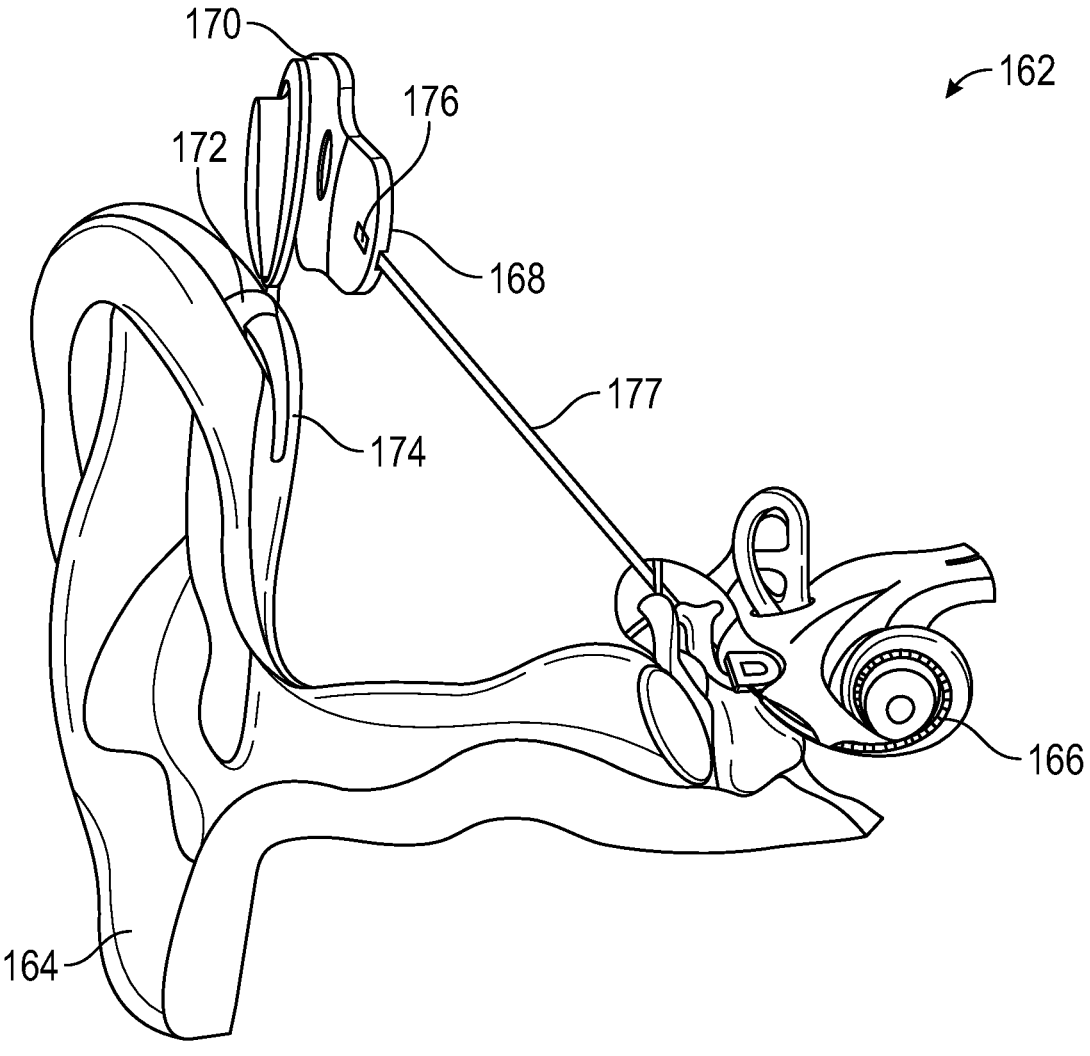

FIG. 23 is a schematic view of a cochlear implant within a patient, where the cochlear implant includes FBR-modulating capabilities according to the present disclosure.

Figure 24:
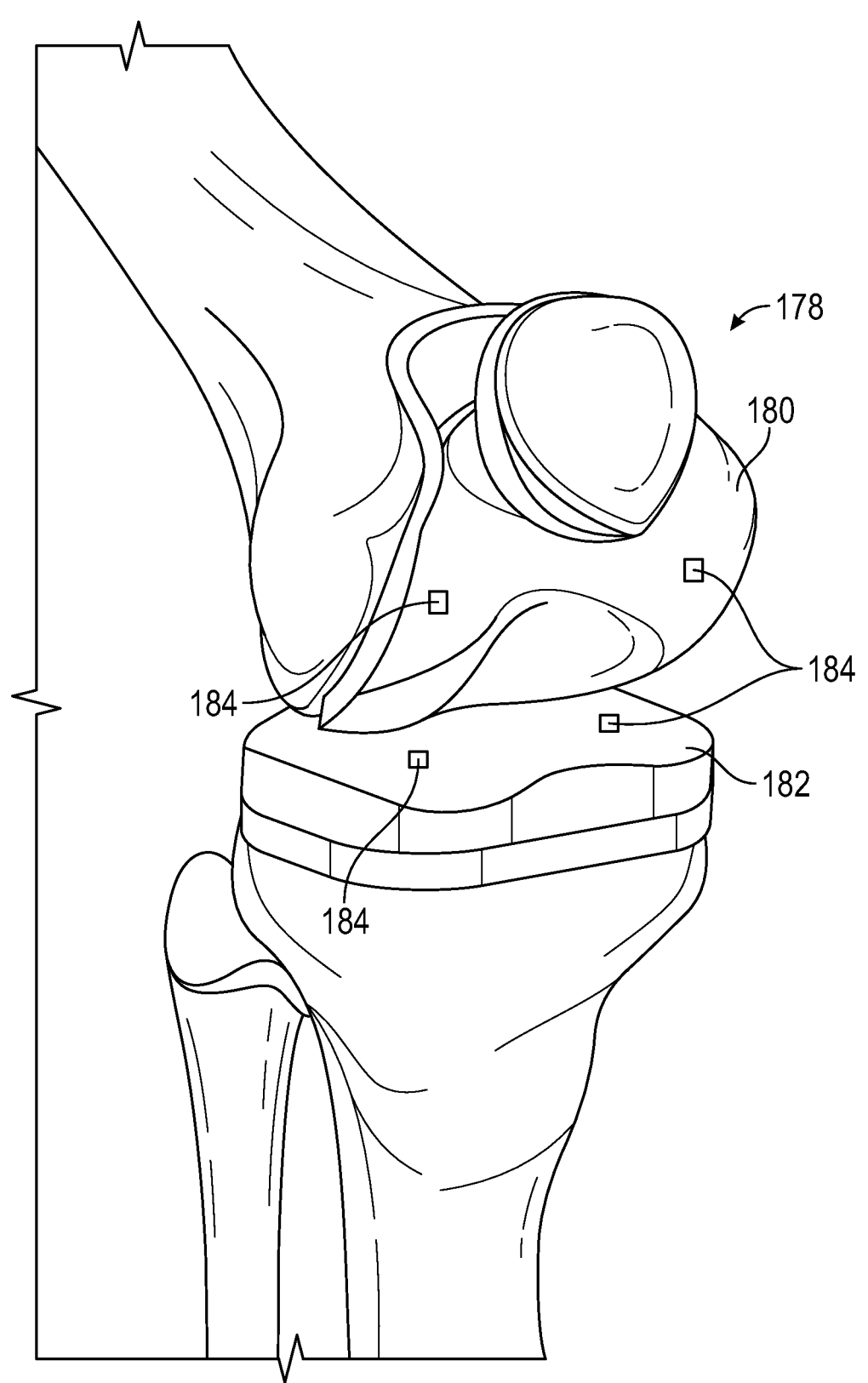

FIG. 24 is a schematic view of an artificial knee that includes FBR-modulating capabilities according to the present disclosure.

Figures 25, 26:
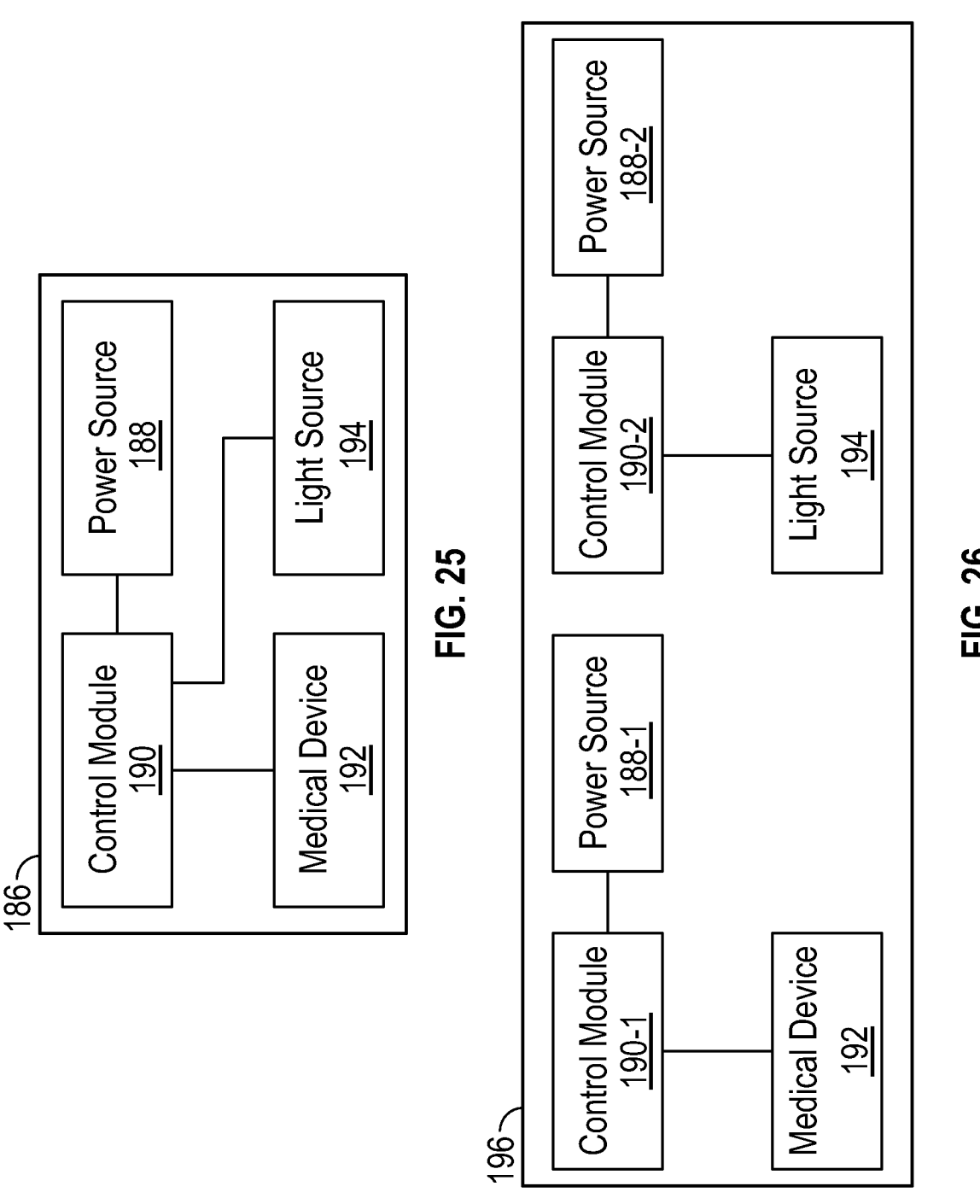

FIG. 25 is a schematic diagram of a control scheme for a device that includes FBR-modulating capabilities according to the present disclosure.

FIG. 26 is a schematic diagram of a control scheme for a device that is similar to the device of FIG. 25, except that operation of the light source is provided separately from other functions of the device.

Figures 27, 28:
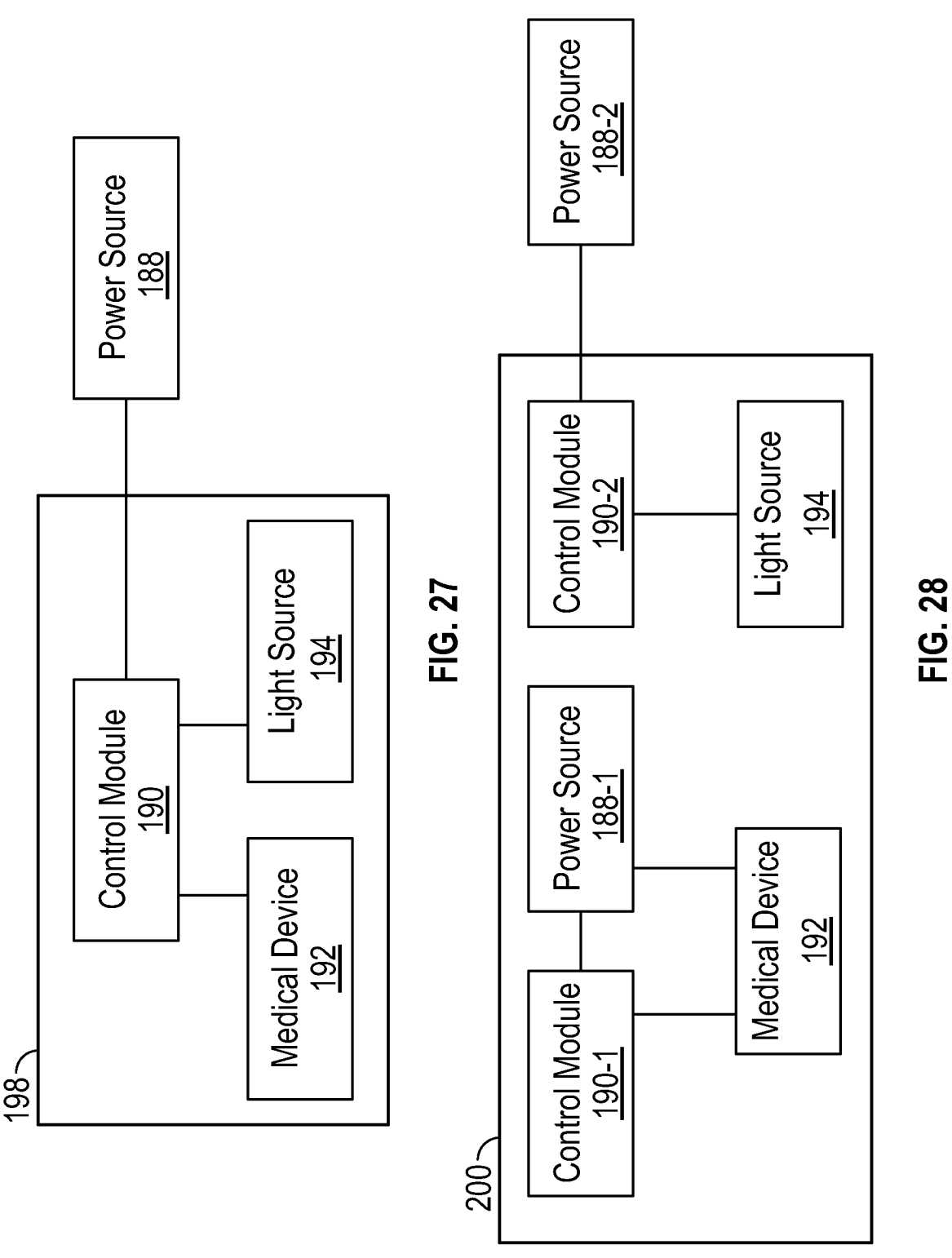

FIG. 27 is a schematic diagram of a control scheme for a device that is similar to the device of FIG. 25, except that at least a portion of the power source is provided remotely from the device.

FIG. 28 is a schematic diagram of a control scheme for a device that is similar to the device of FIG. 26, except that operation of the light source is provided separately from other functions of the device.

DETAILED DESCRIPTION

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Embodiments are described herein with reference to schematic illustrations of embodiments of the disclosure. As such, the actual dimensions of the layers and elements can be different, and variations from the shapes of the illustrations as a result, for example, of manufacturing techniques and/or tolerances, are expected. For example, a region illustrated or described as square or rectangular can have rounded or curved features, and regions shown as straight lines may have some irregularity. Thus, the regions illustrated in the figures are schematic and their shapes are not intended to illustrate the precise shape of a region of a device and are not intended to limit the scope of the disclosure. Additionally, sizes of structures or regions may be exaggerated relative to other structures or regions for illustrative purposes and, thus, are provided to illustrate the general structures of the present subject matter and may or may not be drawn to scale. Common elements between figures may be shown herein with common element numbers and may not be subsequently re-described.

The present disclosure relates generally to modulation of foreign body responses (FBRs) in living tissue, and more particularly, to devices and related methods for light-based modulation of FBRs in living tissue. Light sources are disclosed that provide light with characteristics for modulation of FBRs that may be elicited by percutaneous and/or subcutaneous devices, including medical devices and other consumer electronic devices. Light delivery structures are disclosed that propagate light from such light sources to irradiate associated subcutaneous tissues. Modulation of FBRs may include inhibiting collagen and fibrous tissue generation, modulating inflammation and healing, and/or increasing nitric oxide production and/or release. By modulating FBRs associated with percutaneous and/or subcutaneous devices, performance characteristics and lifetimes of such devices may be improved.

Figure 1A:
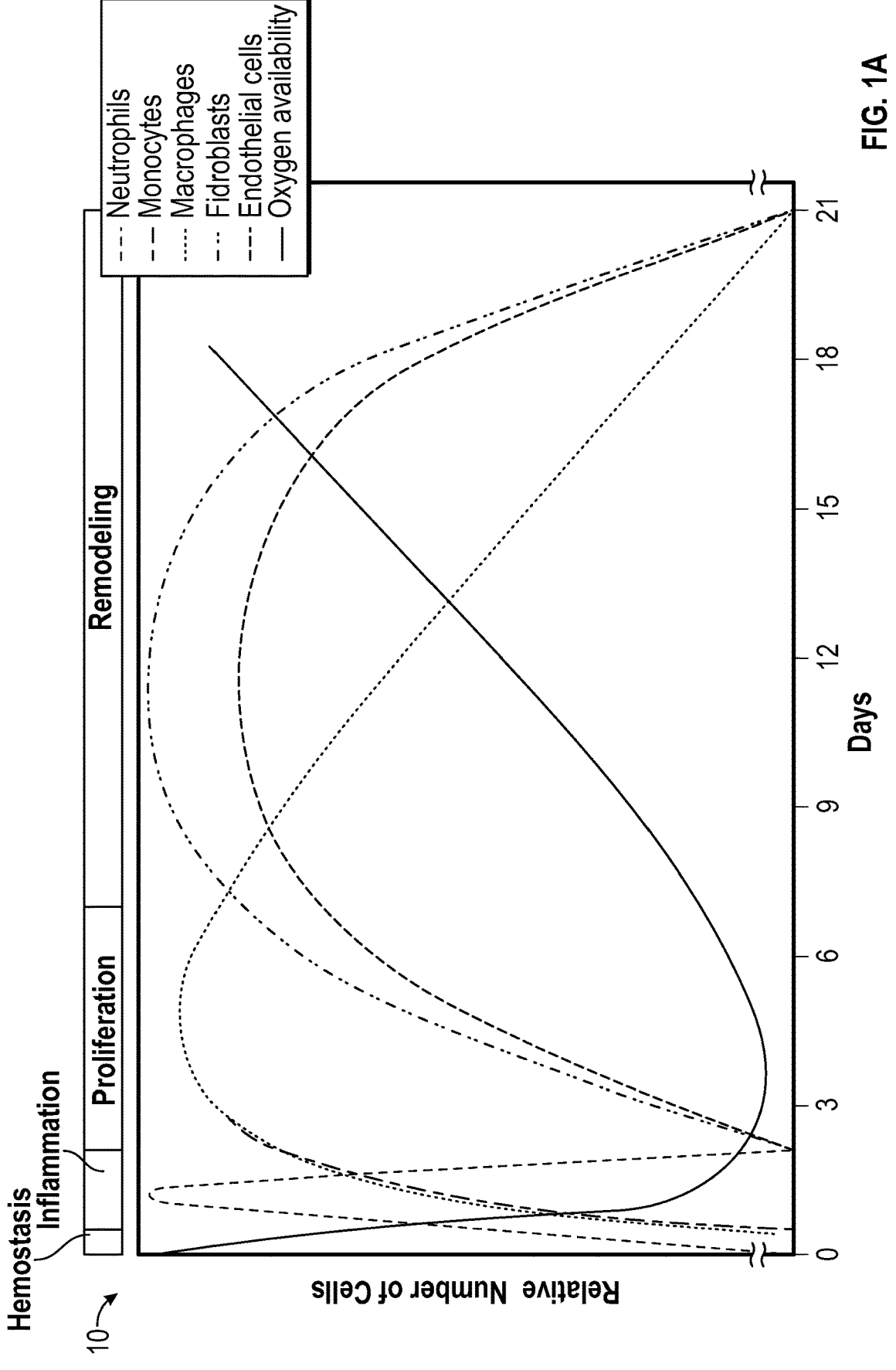
FIG. 1A is a chart that generally illustrates cell proliferation during progression through wound healing phases that may be associated with a foreign body response (FBR).

When a foreign object is inserted within living tissue, an FBR may initiate that cascades through various phases of wound healing over time. Hemostasis is the initial phase that occurs immediately upon insertion of a foreign object whereby clotting is initiated to mitigate blood loss. Hemostasis is followed by an inflammatory phase where localized inflammation may serve to further control bleeding, reduce infection, and prepare the wound for new tissue formation. During proliferation, new tissue forms along the wound site, followed by a remodeling or maturation phase where collagen is remodeled to promote wound closure. In this regard, FIG. 1A is a chart 10 that generally illustrates cell proliferation during progression through wound healing phases that may be associated with an FBR. In the chart 10, relative amounts of various cell types and oxygen availability in associated tissue are plotted by number of days post initiation of the FBR. The chart 10 further provides exemplary timing for hemostasis, inflammation, proliferation, and remodeling phases, although it is expected that exact timing may vary from patient to patient. As illustrated, hemostasis and inflammation stages are marked by a rapid increase in neutrophils that consume available oxygen. As neutrophils decline, monocytes and then macrophages ramp up and further consume oxygen as the tissue transitions to proliferation. The heightened activity of the neutrophils and monocytes are signaling triggers for fibroblasts and endothelial cells that over a longer time duration may eventually close the wound during remodeling. In the case of a foreign body that remains, the resulting tissue may attempt to encapsulate the foreign body, thereby walling it off from surrounding tissue.

In the case of percutaneous and/or subcutaneous objects, such as various medical and consumer electronic devices, associated FBRs can have an impact on device accuracy and/or lifetime. To explore the effect of FBRs on continuous glucose monitors (CGMs), a fifty-two-year-old, non-diabetic male volunteer was fitted with two CGM sensors for a 14-day period. The two CGM sensors were identical sensors that were inserted above the beltline, with one sensor placed left of the midline and the other sensor placed to the right of the midline. The sensors were connected to amperometric potentiostats and were biased to 0.55V with respect to the corresponding reference electrode. The signal generated by the sensors were recorded every two minutes over a duration of two weeks. The volunteer also collected blood glucose values at least twice a day throughout the study with a conventional meter and generic blood glucose strips, and glucose values ranged between 75 milligrams per deciliter (mg/dL) and 125 mg/dL. FIGS. 1B to 1F represent data plots for the two sensors (represented as Sensor 1 and Sensor 2) over the two-week period.

Figure 1B:
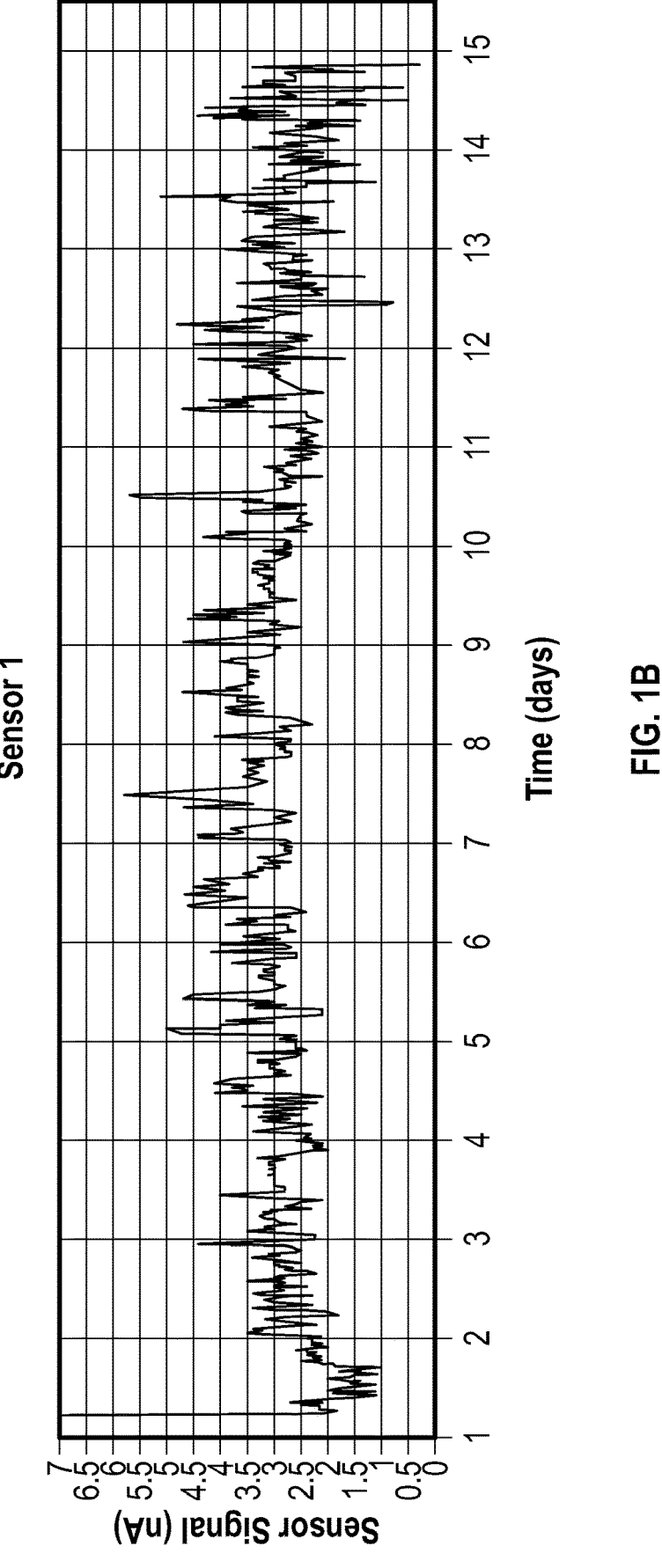
FIG. 1B is a chart of a sensor signal of a first continuous glucose monitor (CGM) over a two-week period for a non-diabetic male volunteer to observe the effects of FBR.
Figure 1C:
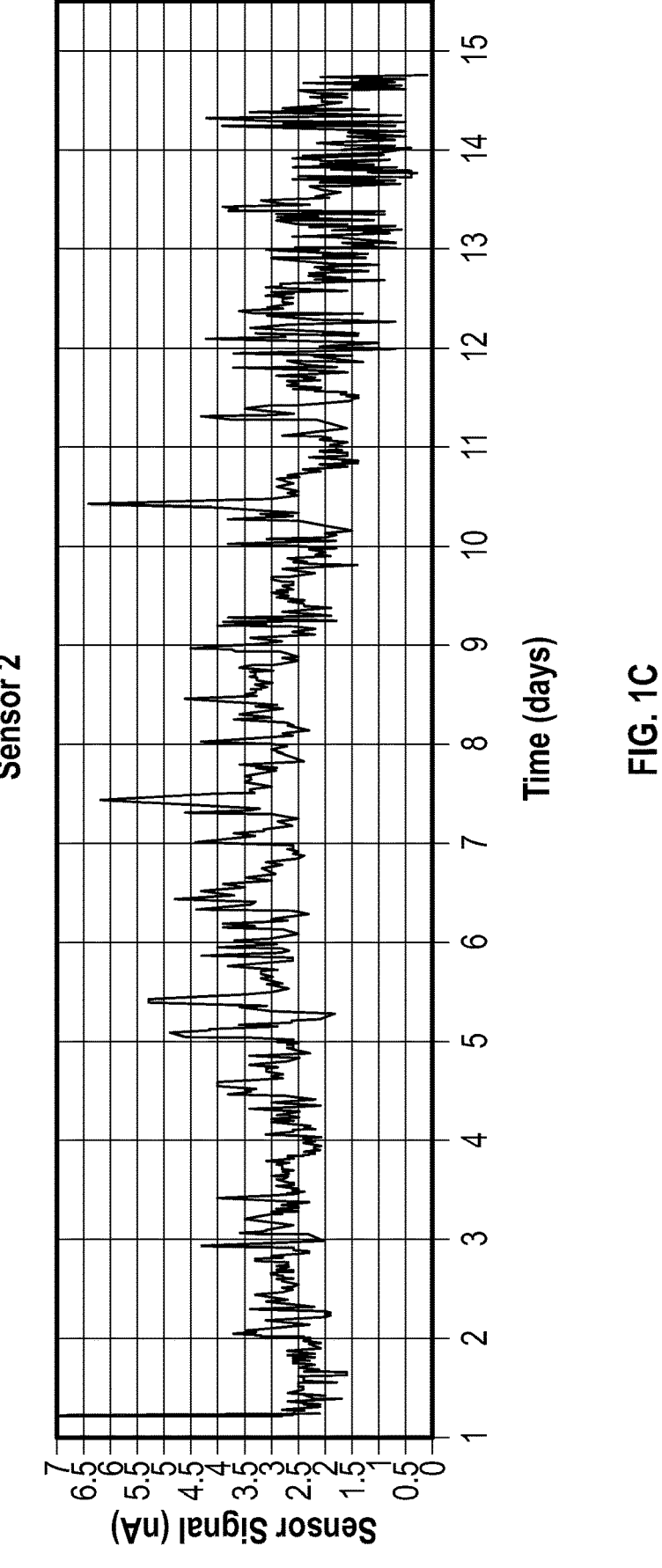
FIG. 1C is a chart of a sensor signal of a second CGM in the same volunteer and over the same two-week period of FIG. 1B.

FIG. 1B is a chart of the Sensor 1 sensor signal in nanoamperes (nA) over the two-week period and FIG. 1C is a chart of the Sensor 2 sensor signal in nA over the same two-week period in the volunteer. As illustrated, sensitivity and signal strength of the sensor signals tends to be low during the first two days, followed by a period where both sensor signals tend to track with one another more precisely. Beyond about 10 days, the sensor signals exhibit increased noise and reduced signal strengths. Such variability in signal strength and sensitivity may be attributed to various FBR stages as described below for FIGS. 1D to 1F.

Figure 1D:
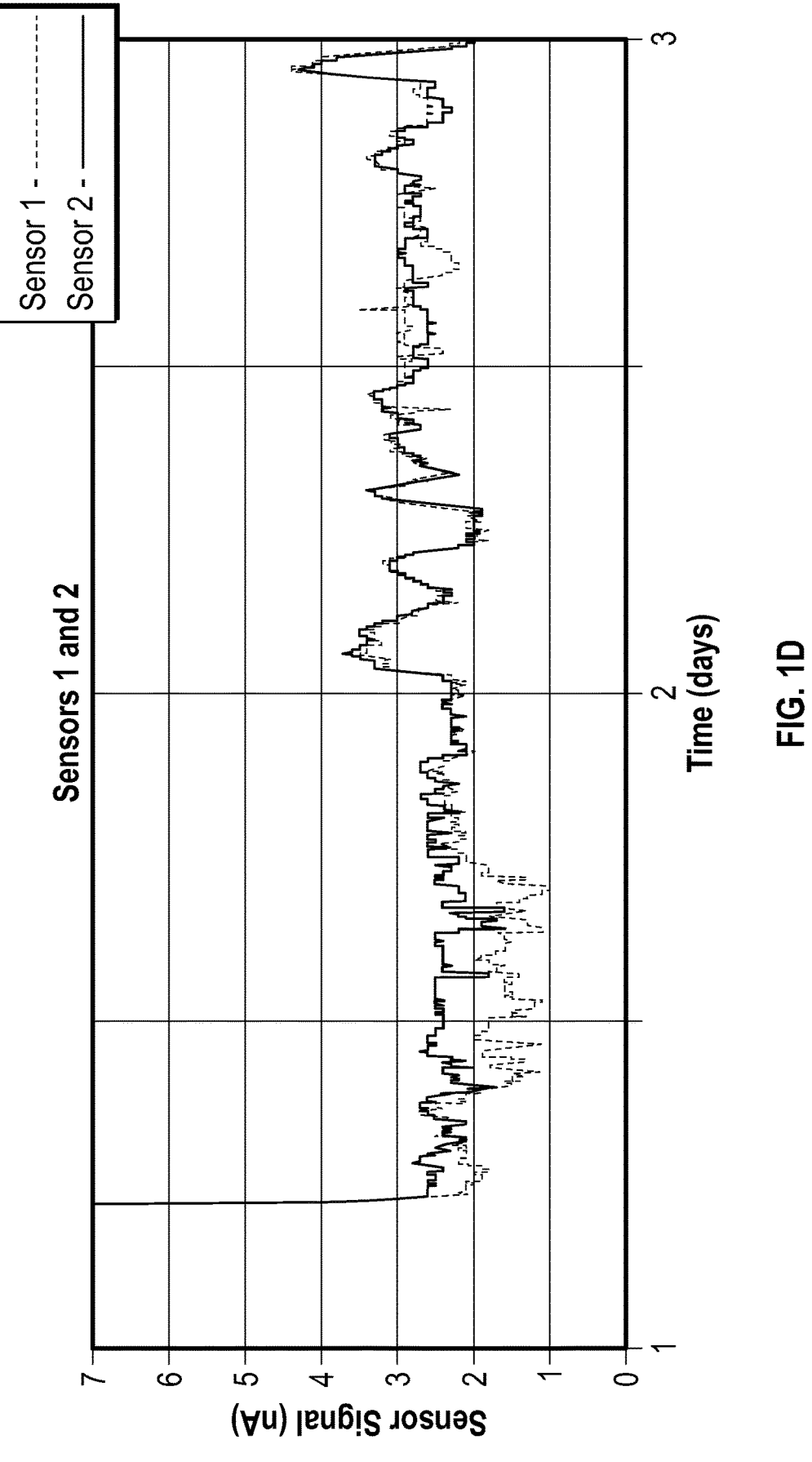
FIG. 1D is a combined chart of sensor signals from the first and second CGMs over the first two days from the charts of FIGS. 1B and 1C.

FIG. 1D is a combined chart of sensor signals from Sensor 1 and Sensor 2 over the first two days from the charts of FIGS. 1B and 1C. During the first two hours after powering on the Sensors 1 and 2, electrochemical break-in may take about 1-2 hours before the signals settle into a range of 1 to 3 nA. While the Sensor 1 and Sensor 2 signals begin to track more closely together by the second day, both sensors still exhibit low sensitivity to actual glucose changes in the volunteer. This may be correspond with one or more portions of the hemostasis and inflammation stages of a FBR as illustrated in FIG. 1A, indicating reduced oxygen availability to the Sensors 1 and 2.

Figure 1E:
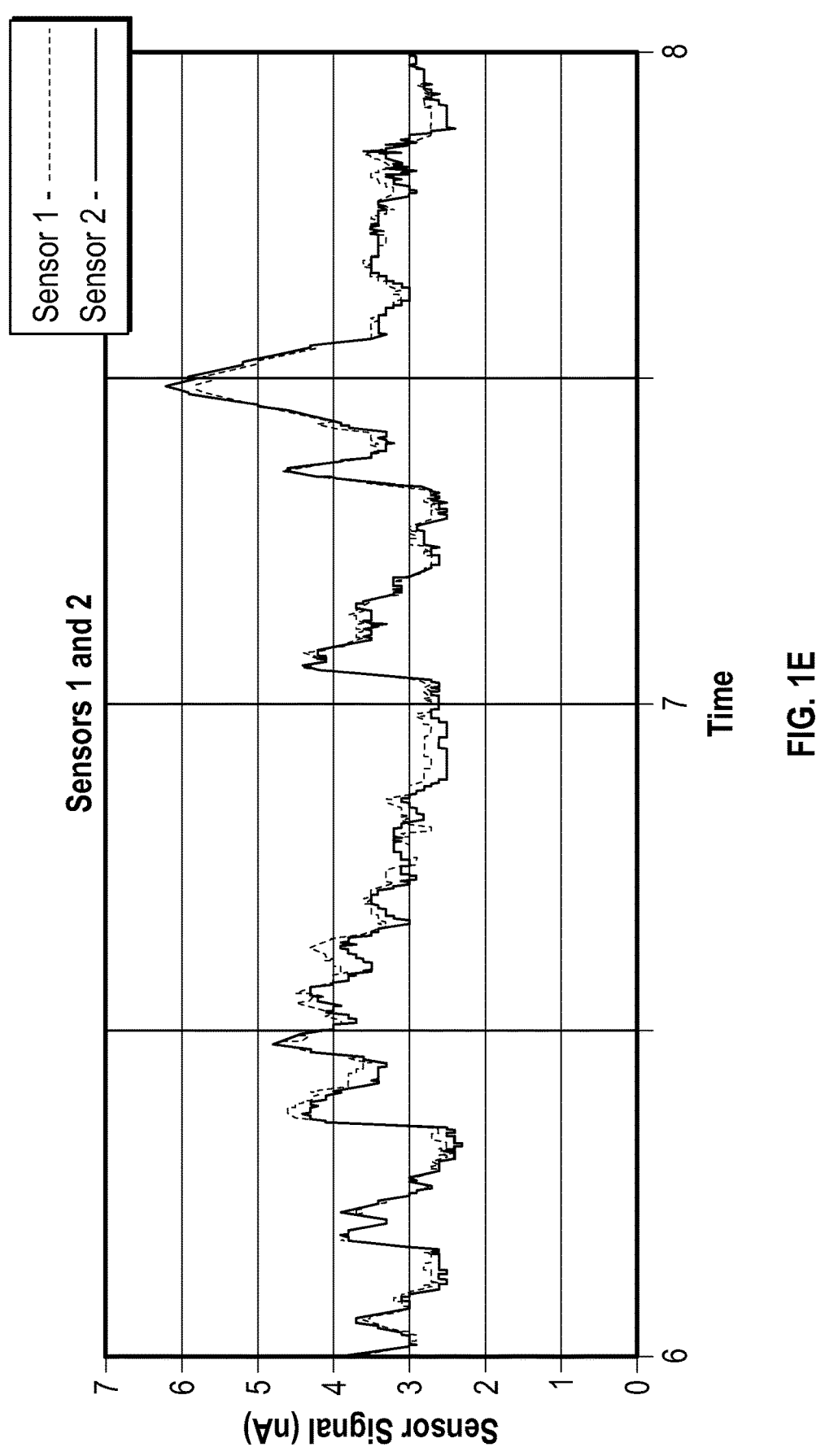
FIG. 1E is a combined chart of sensor signals from the first and second CGMs over days six and seven from the charts of FIGS. 1B and 1C.

FIG. 1E is a combined chart of the sensor signals from Sensor 1 and Sensor 2 over days 6 and 7 from the charts of FIGS. 1B and 1C. As illustrated, both sensors obtain signal strengths in the range of 2 to 5 nA and both track with one another with increased precision and sensitivity and reduced noise, indicating improved accuracy with the volunteer's actual blood glucose values. Turning back to FIG. 1A, this time period may correspond with certain portions of proliferation and early portions of remodeling phases, indicating the FBR response may have reduced impacted on operation of the sensors during this time period.

Figure 1F:
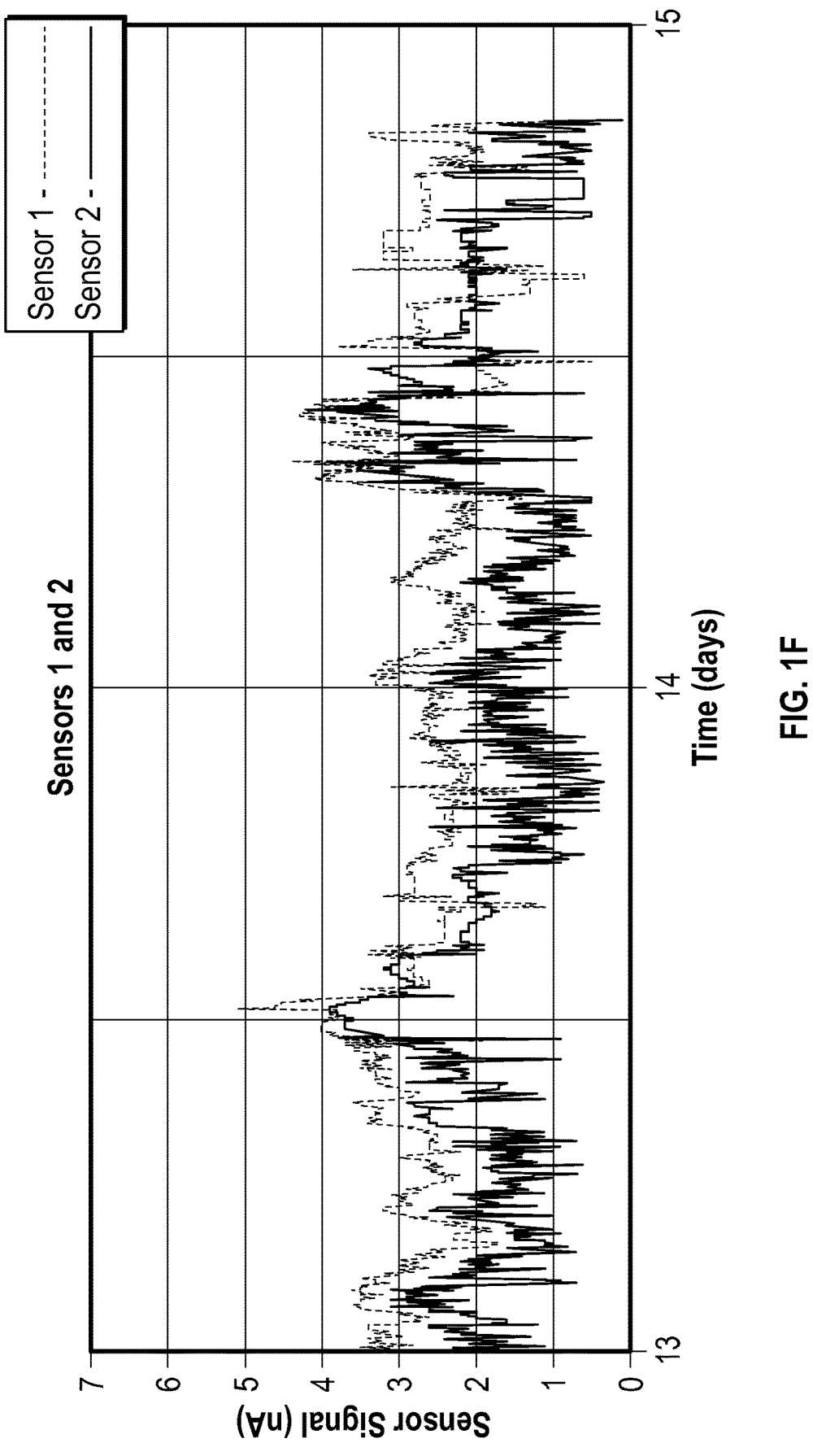
FIG. 1F is a combined chart of sensor signals from the first and second CGMs over days thirteen and fourteen from the charts of FIGS. 1B and 1C.

FIG. 1F is a combined chart of the sensor signals from Sensor 1 and Sensor 2 over days 13 and 14 from the charts of FIGS. 1B and 1C. As illustrated, the signal strengths for both sensors exhibit degradation, with values now ranging from 0.5 to 4 nA, and Sensor 2 exhibits a greater decrease in signal strength than Sensor 1. This degradation in raw signal strength may be attributed to diffusion limitations provided by FBR capsule formation in the remodeling phase. In this regard, both sensors display greater noise with respect to the charts of FIGS. 1D and 1E.

Embodiments of the present disclosure are provided that modulate FBRs for percutaneous and/or subcutaneous objects, such as various medical and consumer electronic devices, with light. By modulating associated FBRs, performance characteristics and operational lifetimes of such devices may be improved. In the example of percutaneous and/or subcutaneous sensors, modulating the associated FBR may enhance sensor accuracy and/or lifetime by altering the mechanisms by which the FBR may attempt to encapsulate the sensor. In the example of CGMs provided in FIGS. 1B to 1E, FBR-modulating light may be delivered to slow down later stages of FBR progression in order to prolong periods of operation like what is shown in FIG. 1E. FBR-modulating light may also be provided to enhance progression through initial FBR stages to reach periods of operation like what is shown in FIG. 1E more quickly. In comparison to actual blood glucose concentrations for glucose monitoring embodiments, FBR modulation according to the present disclosure may provide improved measurement of glucose in the interstitial space by reducing time lag, increasing accuracy, and also lengthening the duration of clinically relevant sensor performance. In the example of subcutaneous implants, other metrics may be useful in determining improvements related to FBR modulation. In the example of an artificial joint replacement, modulating the FBR according to the present disclosure may reduce pain associated with a range of motion in within the joint. Certain aspects of the present disclosure are directed to applications of light for inhibiting collagen and fibrous tissue generation (e.g., inhibiting collagen biosynthesis, inhibiting pro-collagen production, inhibiting collagen proliferation and/or inhibiting collagen relative migration speed), modulating inflammation and healing, and/or increasing endogenous nitric oxide (NO) production and/or release. In certain aspects, the increase in endogenous NO production and/or release in accordance with the present invention may provide one or more favorable effects, whereby angiogenic behavior exhibited by NO may help avoid the avascular encapsulation, localized NO may serve to down-regulate pro-inflammatory cytokine expression, and/or elevated NO concentrations may result in reduced leukocyte adhesion, such that the NO may reduce localization of inflammatory cells at the device-tissue interface and near such interface.

Aspects of the present disclosure relate to administering light to modulate FBR in living tissue. The mechanisms by which certain wavelengths of light are effective may vary, depending on the wavelength that is administered and the particular stage of the associated FBR. Various wavelengths of light may further induce one or more biological effects within or near irradiated tissue, including antimicrobial effects of inactivating microorganisms that are in a cell-free environment and/or inhibiting replication of microorganisms that are in a cell-associated environment, upregulating a local immune response, stimulating enzymatic generation of NO to increase endogenous stores of NO, releasing NO from endogenous stores of NO, and inducing an anti-inflammatory effect. According to aspects of the present disclosure, light may be provided over a wide range of wavelengths, including ultraviolet (UV) ranges, visible light ranges, and infrared (IR) ranges, and combinations thereof to modulate various FBR phases and/or induce other biological effects.

In certain aspects, shorter wavelengths of light in a range from near-UV through various wavelengths of blue-green light may elicit an FBR modulating response with reduced impact on tissue viability. In this manner, applications of light with a peak wavelength in a range from 300 nanometers (nm) to 600 nm, or in a range from 315 nm to 600 nm, or in a range from 400 nm to 600 nm, or in a range from 400 nm to 450 nm may serve to down-regulate collagen biosynthesis and provide anti-proliferative effects in fibroblasts, thereby reducing formation of collagen and scarring along the foreign body. Such wavelengths of light may further provide expression of macrophage inhibitory cytokine-1 (MIC-1) that may limit FBR stages of macrophage activation, thereby disrupting progression through later FBR stages associated with increased fibroblasts. In still further aspects, such wavelengths of light may induce increased endogenous NO production and/or release as described above.

In certain aspects, UV light may be administered as part of FBR-modulating and/or antimicrobial light applications. UV wavelength ranges of light may include UV-A light having a peak wavelength in a range from 315 nm to 400 nm, UV-B light having a peak wavelength in a range from 280 nm to 315 nm, and UV-C light having a peak wavelength in a range from 200 nm to 280 nm. However, overexposure to UV light may lead to cytotoxicity concerns in associated tissue. It may therefore be desirable to use shorter cycles and/or lower doses of UV light than corresponding treatments with only visible light.

In certain aspects, longer wavelengths ranges that are inclusive of red and/or near IR light, such as having a peak wavelength in a range from 600 nm to 1600 nm may also be useful to elicit a different FBR modulating response than the previously described shorter wavelengths of light described above. While the shorter wavelengths listed above may serve to suppress collagen and/or macrophage activation during FBR, longer wavelengths of light may elicit a different response, such as promoting progression to collagen and/or fibrous tissue formation along various stages of healing.

Turning back to FIG. 1A, aspects of the present disclosure may relate to irradiating tissue impacted by a foreign body in order to modulate the associated FBR. One or more combinations of light in one or more wavelength ranges may be irradiated to elicit various combinations of FBR-modulating responses along various stages of wound healing. In one example, light with a peak wavelength in a range from 400 nm to 600 nm, or in a range from 400 nm to 450 nm may be applied during one or more time intervals associated with various FBR stages. The light may be applied to reduce collagen and/or fibrous tissue formation that could otherwise interfere with an intended function of a foreign body, such as sensing for medical device sensors. The light may be applied throughout the FBR stages, or during selected time intervals, such as proliferation and remodeling. In other aspects, devices and related methods may include irradiation with light of different wavelength ranges to modulate the FBR differently in different time intervals. For example, the associated tissue may be irradiated with longer wavelengths of light (e.g., red and/or near IR such as in a range from 600 nm to 1600 nm) during one or more portions of hemostasis and/or inflammation stages to induce initial localized healing, followed by irradiation of near UV and/or blue wavelengths of light (e.g., such as in a range from 315 nm to 600 nm) to disrupt later stages of FBR progression. With reference back to FIGS. 1A-1F, a particular protocol may involve application of the longer wavelength light during a time interval of 0 to 4 days and application of the shorter wavelength light during a time interval of 3 to 30 days. In this regard, the initial localized healing may promote securing the foreign body in place, while disrupting later stages of FBR progression may suppress collagen and/or fibrous tissue formation that may impact an intended function of the foreign body. In still further embodiments, devices and related methods may provide different dosing of FBR-modulating light during the various stages of wound healing. Different dosing of FBR-modulating light may refer to different dose intervals (i.e., time between doses), dose durations (i.e., time of a particular dose), dose locations, and/or different wavelengths. By way of example, near UV and/or blue wavelengths of light may be applied throughout the various stages of wound healing, with longer initial dose intervals and/or shorter initial dose durations during time intervals associated with hemostasis and inflammation stages (e.g., 0 to 3 or 4 days), followed by shorter dose intervals and longer dose durations during time intervals associated with proliferation and remodeling phases (e.g., 3 to 30 days). In still further examples, near UV and/or blue wavelengths may be initially applied during proliferation and remodeling phases with no light of any wavelength being applied during hemostasis and inflammation stages. Stated differently, dosing of light may be increased after an initial time period after insertion of the foreign body, where the initial time interval may embody no light irradiation or a lower dosing of light than the subsequent time interval. In various embodiments, the above-described time intervals for the different wavelengths may involve overlapping intervals or nonoverlapping time intervals, depending on the intended application.

Devices as disclosed herein may include a light source capable of emitting a suitable light spectrum that induces one or more FBR modulating responses. A light spectrum can be represented with a graph of emission intensity versus wavelength of light for any particular light source. In certain aspects, light sources may be provided with light characteristics in the visible spectrum, for example with light emissions with peak wavelengths primarily in a range from 400 nm to 700 nm. Depending on the target application, light characteristics may also include IR or near-IR peak wavelengths at or above 700 nm, or UV peak wavelengths at or below 400 nm. As used herein, light may include visual and non-visual electromagnetic radiation with single or multiple peak wavelengths in a range from 180 nm to 4000 nm. In certain embodiments, light emissions may have a single peak wavelength in a range from 200 nm to 1,000 nm, or in a range from 400 nm to 490 nm, or in a range from 400 nm to 435 nm, or in a range from 400 nm to 420 nm, or in a range from 400 nm to 440 nm, or in a range from 400 nm to 450 nm, or in a range from 420 nm to 440 nm, or in a range from 450 nm to 490 nm, or in a range from 600 nm to 1600 nm, or in a range from 490 nm to 570 nm, or in a range from 510 nm to 550 nm, or in a range from 520 nm to 540 nm, or in a range from 525 nm to 535 nm, or in a range from 528 nm to 532 nm, or in from 630 nm to 670 nm, or in a range from 320 nm to 400 nm, or in a range from 385 nm to 450 nm, or in a range from 350 nm to 395 nm, or in a range from 280 nm to 320 nm, or in a range from 320 nm to 350 nm, or in a range from 200 nm to 280 nm, or in a range from 260 nm to 270 nm, or in a range from 240 nm to 250 nm, or in a range from 200 nm to 225 nm. In further embodiments, light emissions may include multiple peak wavelengths selected from any of the above listed ranges, depending on the target application and desired biological effects.

The term "peak wavelength" is generally used herein to refer to the wavelength that is of the greatest radiometric power of the light emitted by a light emitter. The term "dominant wavelength" may refer to the perceived color of a spectrum, i.e., the single wavelength of light which produces a color sensation most similar to the color sensation perceived from viewing light emitted by the light source (i.e., it is roughly akin to "hue"), as opposed to "peak wavelength", which refers to the spectral line with the greatest power in the spectral power distribution of the light source. Because the human eye does not perceive all wavelengths equally (e.g., it perceives yellow and green light better than red and blue light), and because the light emitted by many solid state light emitters (e.g., LEDs) is actually a range of wavelengths, the color perceived (i.e., the dominant wavelength) is not necessarily equal to (and often differs from) the wavelength with the highest power (peak wavelength). A truly monochromatic light such as a laser may have the same dominant and peak wavelengths. For the purposes of this disclosure, unless otherwise specified herein, wavelength values are discussed as peak wavelength values.

Depending on the target application, full width half maximum (FWHM) values for any of the above-described peak wavelength ranges may be less than or equal to 100 nm, or less than or equal to 90 nm, or less than or equal to 40 nm, or less than or equal to 20 nm. In certain aspects, lower FWHM values are typically associated with single emission color light-emitting diodes (LEDs) in any of the above-described wavelength bands. Larger FWHM values (e.g., from 40 nm to 100 nm) may be associated with phosphor-converted LEDs where spectral bandwidths are a combination of LED emissions and phosphor-converted emissions. Exemplary phosphor-converted LEDs that may be applicable to the present disclosure are phosphor-converted amber LEDs having peak wavelengths in a range from 585 nm to 600 nm and FWHM values in a range from 70 nm to 100 nm, and phosphor-converted mint and/or lime LEDs having peak wavelengths in a range from 520 nm to 560 nm. Additional embodiments of the present disclosure may also be applicable to broad spectrum white LEDs that may include an LED with a peak wavelength in a range from 400 nm to 470 nm, and one or more phosphors to provide the broad emission spectrum. In such embodiments, a broad spectrum LED may provide certain wavelengths that induce one or more biological effects while also providing broad spectrum emissions to the target area for illumination. In this regard, light impingement on tissue for single and/or multiple biological effects may be provided with light of a single peak wavelength or a combination of light with more than one peak wavelength.

Doses of light to induce one or more FBR-modulating and/or other biological effects may be administered with one or more light characteristics, including peak wavelengths, radiant flux, and irradiance to target tissues. Irradiances to target tissues may be provided in a range from 0.1 milliwatts per square centimeter ($mW/cm^2$) to 200 $mW/cm^2$, or in a range from 5 $mW/cm^2$ to 200 $mW/cm^2$, or in a range from 5 $mW/cm^2$ to 100 $mW/cm^2$, or in a range from 5 $mW/cm^2$ to 60 $mW/cm^2$, or in a range from 60 $mW/cm^2$ to 100 $mW/cm^2$, or in a range from 100 $mW/cm^2$ to 200 $mW/cm^2$. Such irradiance ranges may be administered in one or more of continuous wave and pulsed configurations, including LED-based photonic devices that are configured with suitable power (radiant flux) to irradiate a target tissue with any of the above-described ranges. A light source for providing such irradiance ranges may be configured to provide radiant flux values from the light source of at least 5 mW, or at least 10 mW, or at least 15 mW, or at least 20 mW, or at least 30 mW, or at least 40 mW, or at least 50 mW, or at least 100 mW, or at least 200 mW, or in a range of from 5 mW to 200 mW, or in a range of from 5 mW to 100 mW, or in a range of from 5 mW to 60 mW, or in a range of from 5 mW to 30 mW, or in a range of from 5 mW to 20 mW, or in a range of from 5 mW to 10 mW, or in a range of from 10 mW to 60 mW, or in a range of from 20 mW to 60 mW, or in a range of from 30 mW to 60 mW, or in a range of from 40 mW to 60 mW, or in a range of from 60 mW to 100 mW, or in a range of from 100 mW to 200 mW, or in a range of from 200 mW to 590 mW, or in another range specified herein. Depending on the configuration of one or more of the light sources, the corresponding illumination device, and the distance away from a target tissue, the radiant flux value for the light source may be higher than the irradiance value at the tissue.

While certain peak wavelengths for certain target tissue types may be administered with irradiances up to 200 $mW/cm^2$ without causing significant tissue damage, safety considerations for other peak wavelengths and corresponding tissue types may require lower irradiances, particularly in continuous wave applications. In certain embodiments, pulsed irradiances of light may be administered, thereby allowing safe application of significantly higher irradiances. Pulsed irradiances may be characterized as average irradiances that fall within safe ranges, thereby providing no or minimal damage to the applied tissue. In certain embodiments, irradiances in a range from 0.1 $W/cm^2$ to 10 $W/cm^2$ may be safely pulsed to target tissue.

Light sources may include one or more of LEDs, organic LEDs (OLEDs), lasers and other lamps according to aspects of the present disclosure. Lasers may be used for irradiation in combination with optical fibers or other delivery mechanisms. LEDs are solid state electronic devices capable of emitting light when electrically activated. LEDs may be configured across many different targeted emission spectrum bands with high efficiency and relatively low costs. Accordingly, LEDs may be used as light sources in photonic devices for phototherapy applications. Light from an LED is administered using a device capable of delivering the requisite power to a targeted treatment area or tissue. High power LED-based devices can be employed to fulfill various spectral and power needs for a variety of different medical applications. LED-based photonic devices described herein may be configured with suitable power to provide irradiances as high as 100 $mW/cm^2$, or 200 $mW/cm^2$ in the desired wavelength range. An LED array in this device can be incorporated into an irradiation head, hand piece and/or as an external unit.

In addition to various sources of light, the principles of the present disclosure may also include one or more other types of directed energy sources. As used herein, a directed energy source may include any of the various light sources previously described, and/or an energy source capable of providing one or more of heat, IR heating, resistance heating, radio waves, microwaves, soundwaves, ultrasound waves, electromagnetic interference, and electromagnetic radiation that may be directed to a target body tissue. Combinations of visual and non-visual electromagnetic radiation may include peak wavelengths in a range from 180 nm to 4000 nm. Illumination devices as disclosed herein may include a light source and another directed energy source capable of providing directed energy beyond visible and UV light. In other embodiments, the other directed energy source capable of providing directed energy beyond visible and UV light may be provided separately from illumination devices of the present disclosure.

Certain aspects of the present disclosure relate to devices and corresponding methods for advantageously modulating the FBR for continuous glucose monitors (CGMs). By providing CGMs that are less susceptible to adverse FBR-related effects, associated sensors may maintain their accuracy for relatively longer time periods than conventional CGMs. For example, in comparison to actual blood glucose concentrations, measurement of glucose in the interstitial space may be improved by reducing time lag, increasing accuracy, and also lengthening the duration of clinically relevant sensor performance when modulating FBR according to the present disclosure. Before delving further into aspects of the present disclosure, a general discussion of CGMs is provided. Enzymatic oxidation of glucose to gluconolactone (which hydrolyzes to gluconic acid) may occur in the presence of catalyzing glucose oxidase (GOx), and subsequent electrochemical detection of oxygen depletion and/or hydrogen peroxide formation may be performed by way of CGM sensors. The enzymatic oxidation of glucose to gluconolactone (which hydrolyzes to gluconic acid) in the presence of catalyzing GOx, with subsequent electrochemical detection of oxygen depletion and/or hydrogen peroxide formation is shown in the schematic diagram 12 of FIG. 2. Some sensors may detect glucose by monitoring the consumption of oxygen using two oxygen electrodes (one covered with the enzyme and one for reference). The differential current between these electrodes can be compared so as to correct for background variations in oxygen. Alternatively, hydrogen peroxide produced enzymatically by GOx can be quantified amperometrically. Amperometric enzyme electrodes vary greatly in electrode design, electrode material, enzyme immobilization method, and polymeric membrane compositions. A variety of devices and materials have been employed for carrying out glucose concentration measurements in percutaneous CGM devices. CGM devices typically include a needle-type sensor, or sensor probe, that is designed such that a distal end of the sensor resides percutaneously.

FIG. 3 is an illustration showing a portion of a device 14 that includes a foreign body 16 for percutaneous placement through skin 18 of a host and further includes FBR-modulating capabilities according to principles of the present disclosure. In certain embodiments, the device 14 may comprise a CGM with the foreign body 16 representing a sensor probe of the CGM. As illustrated, a light source 20 may be provided outside the skin 18 in an arrangement to irradiate light 22 to and through portions of the host's skin 18 that are registered with a region of subcutaneous tissue where the foreign body 16 is inserted. The light source 20 may embody a single type of light source or multiple light sources capable of independently providing different wavelengths at different times. Depending on the wavelength, portions of the light 22 may penetrate the skin 18 to irradiate underlying tissue at various depths. However, not all wavelengths of light 22 are suitable for passing through the skin 18 and underlying tissue. For example, red and near IR wavelengths may pass to certain tissue depths (e.g., up to about 2.5 millimeters (mm)) under the skin 18 and shorter wavelengths, such as blue, may have very little light that passes through tissue depths beyond about 0.5 mm. In typical CGM applications, the sensor probe may extend to depths of in a range from about 3 mm to about 15 mm, or in range from about 4 mm to 8 mm, or in a range from about 5 mm to 7 mm beneath the skin 18 depending on the application and angle of insertion. In this regard, the sensor probe (e.g., the foreign body 16) may pass through the epidermis and dermis so that a distal end 16' of the sensor probe may reside in the subcutaneous tissue layer for glucose monitoring of interstitial fluid. Accordingly, the arrangement illustrated in FIG. 3 may be suitable for delivery of longer wavelengths of light 22 to the skin 18 and at certain depths below the skin 18 when it is desired to modulate FBR by promoting increased healing along the foreign body 16, such as during portions of hemostasis and/or inflammation stages.

Even with longer wavelengths, the light 22 may still not penetrate deep enough to reach a distal end 16' of the foreign body 16. However, this may be advantageous for certain applications, such as CGMs. Active sensing regions for sensor probes in glucose monitoring may be arranged at or near the distal end 16' as illustrated in FIG. 3. Optical absorbance of glucose and glucose oxidase may be higher in the range of 560 nm to 760 nm with a peak absorbance around 660. Additionally, absorbance may start to increase below 420 nm. In this regard, it may be desirable to avoid wavelengths with higher absorbances from interacting with the active sensing region. To the extent that some light does reach the active sensing region, such effects may be compensated for based on the spectra of light employed, the irradiance flux density of light delivered, and the duration of such light delivery.

FIG. 4 is an illustration showing a portion of a device 24 that includes delivery of light 22 at increased tissue depths beneath the skin 18 to provide FBR-modulating capabilities according to principles of the present disclosure. In certain embodiments, the light source 20 may be arranged to irradiate light 22 underneath a host's skin 18 in order to reach subcutaneous tissue portions along or near the foreign body or sensor probe 16. For example, a light delivery structure 26, such as an optical waveguide, may be inserted percutaneously underneath the skin 18 and light 22 may propagate from the light source 20 to irradiate tissue at a depth that is near a targeted region of the foreign body 16. In certain embodiments, the light delivery structure 26 comprises an optical waveguide in the form of a fiber optic. For CGM applications, the arrangement of the light delivery structure 26 may provide suitable delivery of shorter wavelengths of light, including blue, blue-green, and/or near-UV, to targeted regions of the sensor probe that correspond where active sensing occurs. In still further embodiments, the light delivery structure 26 may provide suitable delivery of longer wavelengths of light, such as the red and/or near IR wavelengths described above, alone or in combination with the shorter wavelengths of light. Corresponding tissue depths may be in a range from 1 mm to 15 mm, or in a range from 4 mm to 15 mm, depending on the location of the active sensing region. For example, in certain embodiments, an exemplary sensor probe 16 for a CGM may have a sensing region that is arranged at or near the distal end 16' of the sensor probe 16 that is provided at a tissue depth in a range from 4 mm to 8 mm. In this manner, the light delivery structure 26 may be inserted percutaneously to a depth such that the light 22 is delivered in close proximity to the sensing region, such as within about 0.5 mm of the active sensing region. In certain probe tip designs, the sensing region may be provided at a distance of about 1 mm from the distal end 16', or probe tip of the sensor probe 16.

FIG. 5 is an illustration of a portion of a device 28 that includes a combination of FBR-modulating capabilities as described for the device 14 of FIG. 3 and the device 24 of FIG. 4. In this manner, the principles described above for FIGS. 3 and 4 may be incorporated together for the device 28. As illustrated, a first light source 20-1 may be arranged to deliver light 22-1 through the light delivery structure 26 to irradiate tissues at or near the foreign body 16 at various tissue depths beneath the skin 18. A second light source 20-2 may be arranged to irradiate light 22-2 to a surface of the skin 18 and at shallower tissue depths beneath the skin 18, depending on the particular wavelength of the light 22-2. For a CGM application, the first light source 20-1 may provide associated light 22-1 with shorter wavelengths, including blue, blue-green, and/or near-UV while the second light source 20-2 may provide associated light 22-2 with longer wavelengths, such as red and/or near IR. While the particular wavelengths described above may be suitable for certain embodiments, the configuration of the device 28 enables tailored applications that provide different combinations of wavelengths based on different intended FBR-modulating responses. For example, the first and second light sources 20-1, 20-2 may be configured to provide the same wavelength of light to the respective locations above and beneath the skin 18.

The devices of FIGS. 3-5 may be capable of delivering different dosing of FBR-modulating light during the various stages of wound healing illustrated in FIG. 1A. As stated above, different dosing of FBR-modulating light may refer to different dose intervals, dose durations, dose locations, and/or different wavelengths. In a particular dosing protocol, a device and related method for delivery of FBR-modulating light may include providing light with a first wavelength in a range from 600 nm to 1600 nm from insertion of the foreign body 16 up to day 3 during hemostasis and inflammation stage. In a subsequent step, light with a second wavelength that is different than the first wavelength, such as in a range from 400 nm to 600 nm may be provided from day 3 to an end of an operation of the foreign body 16. In further dosing protocols, application times of the first wavelength and the second wavelength may overlap. In still further dosing protocols, a single wavelength in a range from 400 nm to 600 nm may be applied from insertion of the foreign body 16 up to an end of an operation of the foreign body 16. In such protocols, the dosing of the single wavelength may be constant throughout the FBR stages or dosing of the single wavelength may be varied based on the particular FBR stage as previously described.

In certain embodiments, arrangements for delivery of FBR-modulating light may be incorporated as an element within an overall device that includes a percutaneous foreign body, such as a sensor probe of a CGM. Light delivery structures may be arranged to provide light to certain depths beneath the skin, externally to certain surfaces of the skin, and combinations thereof. For delivery of light beneath the skin, corresponding light delivery structures may be arranged to be inserted within the skin concurrently with the foreign body or separately from the foreign body. For concurrent insertion, light delivery structures may be arranged to surround one or more portions of foreign bodies and/or light delivery structures may be provided adjacent corresponding foreign bodies, such as within a region of subcutaneous tissue where a foreign body resides. By incorporating light delivery structures together with foreign bodies, alignment of light delivery structures may be improved in order to more consistently deliver light to targeted areas of the foreign body.

Figure 6:
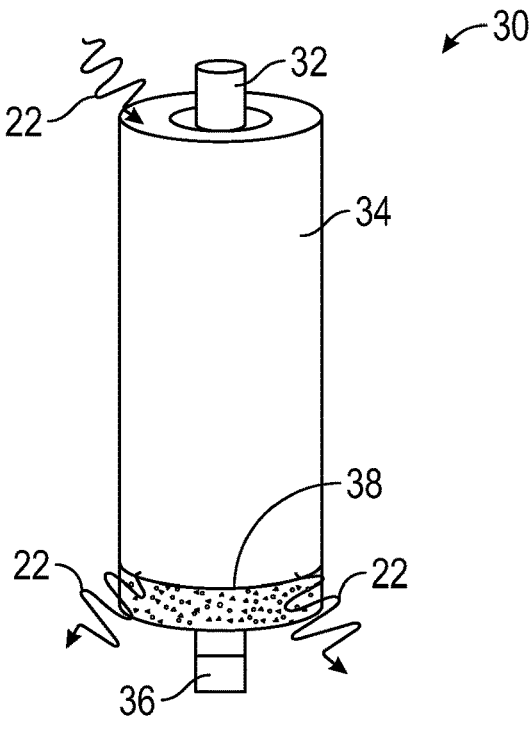
FIG. 6 is an illustration of a portion of a device with a sensor probe and a corresponding light delivery structure for percutaneous insertion in a host to provide FBR-modulating capabilities.

FIG. 6 is an illustration of a portion of a device 30 with a sensor probe 32 and a corresponding light delivery structure 34 for percutaneous insertion in a host to provide FBR-modulating capabilities. In certain embodiments, the device 30 may embody a medical sensing device, such as a CGM, or various other consumer electronic monitoring devices. As illustrated, the light delivery structure 34 embodies a hollow structure that is arranged to surround portions of the sensor probe 32. For example, the light delivery structure 34 may comprise at least one of a sleeve, a film, and a coating that is provided around portions of the sensor probe 32. A portion of the sensor probe 32 that includes an active sensing region 36 is arranged to protrude from an end of the light delivery structure 34. The active sensing region 36 may correspond with a portion of the sensor probe 32 where an electrode is not covered by insulation. When inserted percutaneously, accuracy of the active sensing region 36 may be compromised as an associated FBR advances though various stages. To modulate the FBR, the light delivery structure 34 is arranged to deliver light 22 percutaneously at or near the active sensing region 36. In certain embodiments, the light delivery structure 34 comprises an optical waveguide that is hollow in order to accommodate portions of the sensor probe therethrough. The light delivery structure 34 may further comprise a light-scattering region 38 arranged at an end that is adjacent the active sensing region 36. The light-scattering region 38 may include light-scattering particles or light-diffusing materials that serve to scatter the light 22 that exits the light delivery-structure 34 with improved uniformity across the active sensing region 36. The light-scattering region 38 may embody a coating or film on the light-delivery structure 34 or the light-scattering region 38 may be formed internal to the light-delivery structure 34.

Figure 7:
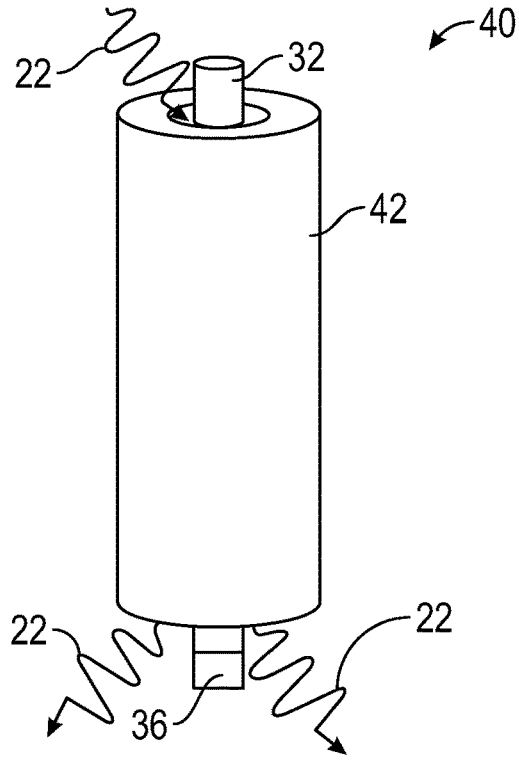
FIG. 7 is an illustration of a portion of a device that is similar to the device of FIG. 6, except the light delivery structure embodies a hollow sheath where light is configured to propagate between the light delivery structure and the sensor probe.

FIG. 7 is an illustration of a portion of a device 40 that is similar to the device 30 of FIG. 6, except a light delivery structure 42 of the device 40 embodies a hollow sheath where light 22 is configured to propagate between the light delivery structure 42 and the sensor probe 32. As illustrated, the sensor probe 32 extends through a space defined by the light delivery structure 42. Light 22 may be directed into a gap formed between the sensor probe 32 and the light delivery structure 42, and the light 22 may exit in a tissue region that includes the active sensing region 36 for modulating an associated FBR. In certain embodiments, the light delivery structure 42 may embody a hollow reflective tube or a hollow light guide for propagation of the light 22. In certain embodiments, the light delivery structure 42 may further include a light-scattering region as described above for FIG. 6.

Figure 8:
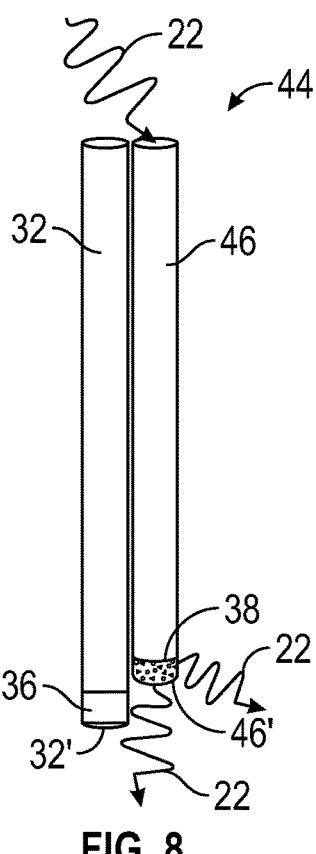
FIG. 8 is an illustration of a portion of a device where a light delivery structure is arranged adjacent to the corresponding sensor probe for percutaneous insertion in a host to provide FBR-modulating capabilities.

FIG. 8 is an illustration of a portion of a device 44 where a light delivery structure 46 is arranged adjacent to the corresponding sensor probe 32 for percutaneous insertion in a host to provide FBR-modulating capabilities. As illustrated, the light delivery structure 46 may be arranged adjacent to the sensor probe 32 and a distal end 46' of the light delivery structure 46 may be offset with a distal end 32' of the sensor probe 32. In this manner, light 22 that exits the light delivery structure 46 may be provided to a region of tissue that also includes the active sensing region 36 for modulation of an associated FBR. The light delivery structure 46 may comprise an optical waveguide, such as a fiber optic. In certain embodiments, the light delivery structure 46 may be attached to the sensor probe 32 for concurrent percutaneous insertion. In other embodiments, the light delivery structure 46 may be spaced from the sensor probe 32. In such an arrangement, the light delivery structure 46 and the sensor probe 32 may be secured to common portions of the device 44 for concurrent percutaneous insertion. In still further embodiments, the light delivery structure 46 and the sensor probe 32 may be secured to different elements of the device 44 for either concurrent percutaneous insertion or percutaneous insertion at different times. Additionally, the light delivery structure 46 and the sensor probe 32 may be aligned parallel with respect to each other or in an angled manner to deliver the light 22 to the active sensing region 36. The light delivery structure 46 may further include a light-scattering region as described above for FIG. 6.

Figure 9:
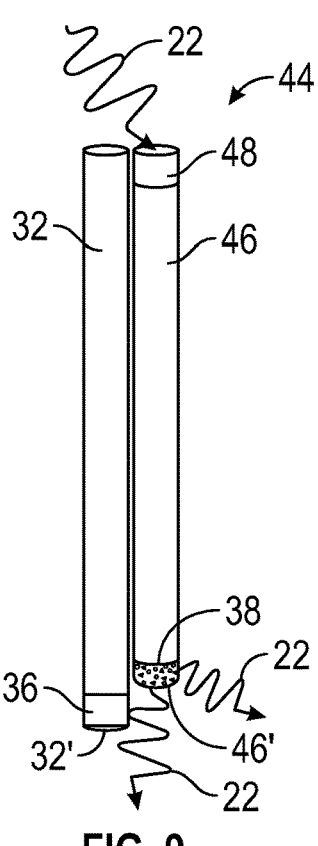
FIG. 9 is an illustration of a portion of the device of FIG. 8 with an arrangement that further includes a light filter associated with the light delivery structure.

FIG. 9 is an illustration of a portion of the device 44 of FIG. 8 with an arrangement that further includes a light filter 48 associated with the light delivery structure 46. In certain embodiments, the light filter 48 may be positioned between a light source that delivers the light 22 and the distal end 46' of the light delivery structure 46 for attenuating certain wavelengths of the light 22. The light filter 48 may be incorporated within the light delivery structure 46 or the light filter 48 may embody a separate structure that is positioned at a light-receiving end of the light delivery structure 46. The light filter 48 may be configured to filter certain wavelengths of the light 22 while allowing other wavelengths of the light 22 to propagate therethrough and toward the distal end 46'. For example, the light filter 48 may embody a low-pass filter that filters wavelengths above a particular value, a high-pass filter that filters wavelengths below a particular value, a bandpass filter that passes wavelengths that are within a particular wavelength band, and a notch filter that rejects wavelengths that are within a particular wavelength band. In this manner, the light delivery structure 46 may be configured to further tailor received light 22 so that only a desired wavelength or a desired wavelength range is allowed through the remaining portion of the light delivery structure 46. By way of example, for applications where it is desired to deliver shorter wavelengths of light to the active sensing region 36, the light filter 48 may be configured to filter at least 50 percent, or at least 80 percent of the light 22 that may be in a wavelength range from 590 nm to 1,000 nm, or in a range from 590 nm to 600 nm. In still further examples, one or more light filters 48 may be provided to filter shorter wavelengths of the light 22, such as one or more wavelengths within the UV spectrum. In this regard, the use of one or more light filters 48 may allow a user to tailor specific wavelengths of light for a particular application without necessarily having to change the corresponding light source.

While FIGS. 6-9 are described in the context of a sensor probe 32, such as a sensor probe for a CGM, the principles disclosed are applicable to any foreign body (e.g., 16 in FIGS. 3-5) that may be inserted percutaneously. As disclosed herein, foreign bodies may include an enzymatic electrochemical glucose sensor, a non-enzymatic electrochemical sensors, a microsensor or microsensor array that monitors hydrogen peroxide production amperometrically as a measure of the glucose concentration, an implantable microdialysis probe, a catheter, an intravenous line, a chemotherapy port, a lactate biosensor, a cancer biosensor, an glycated hemoglobin or A1C biosensor, a NO concentration detector, a percutaneous electric nerve stimulation (PENS) device, and any percutaneous device that must access bodily tissues and or fluids in order to perform its intended function.

For examples where the foreign body is a lactose biosensor, lactose biosensing may be based on lactate oxidase and palladium benzoporphyrin immobilized in hydrogels. I-Lactate is an analyte of significant interest due to its role in sports medicine, clinical chemistry, and overall normal metabolic function. Lactate is a normal byproduct of cellular metabolism. However, intracellular lactate concentrations increase during anaerobic respiration, and interstitial lactate levels increase as it is excreted by cells, and it can accumulate in muscles and other tissues to cause soreness, pain, and impaired function. Lactate concentrations can be used to assess a variety of acute deoxygenation events including hypovolemia (shock), heart disease, and renal failure. High lactate levels are also commonplace in traumatic injury, where a patient has undergone significant blood loss. The ability to monitor blood lactate levels can improve identification of patients requiring resuscitative care when compared to standard blood pressure monitoring. In certain embodiments, continuous lactate monitoring is used for dynamic health assessment of active-duty military and other high-risk personnel, or to approximate "oxygen debt" in endurance athletes. In certain embodiments, a lactate biosensor uses an enzyme to produce hydrogen peroxide ($H_2O_2$) at the surface of a percutaneously inserted electrode, and the resulting change in electric potential can be correlated to interstitial lactate concentrations. As with any foreign body, a challenge associated with percutaneous monitoring of lactate levels relates to a foreign body response elicited by implantation of the lactate sensor. In this regard, the principles of the present disclosure may advantageously provide FBR-modulating capabilities to mitigate the foreign body response on lactate sensor functions, thereby improving accuracy and extending the useful lifetime of such devices.

In certain embodiments, a foreign body as disclosed herein may comprise a cancer biosensor. Significant efforts have been made to detect biomarkers of cancers, such as breast and lung cancer. In this regard, cancer biosensors may provide a relatively non-invasive way to detect cancer progression. Cancer biosensors may include specific biorecognition molecules such as antibodies, complementary nucleic acid probes or other immobilized biomolecules on a transducer surface. The biorecognition molecules interact specifically with the biomarkers (targets) and the generated biological responses are converted by the transducer into a measurable analytical signal. Depending on the type of biological response, various transducers can be used to fabricate cancer biosensors, including electrochemical, optical and mass-based transducers. As with other foreign bodies, challenges associated with percutaneous monitoring with cancer biosensors may involve the elicited foreign body response. In this regard, the principles of the present disclosure may advantageously provide FBR-modulating capabilities to mitigate the foreign body response on cancer sensor functions, thereby improving accuracy and extending the useful lifetime of such devices.

Figure 10A:
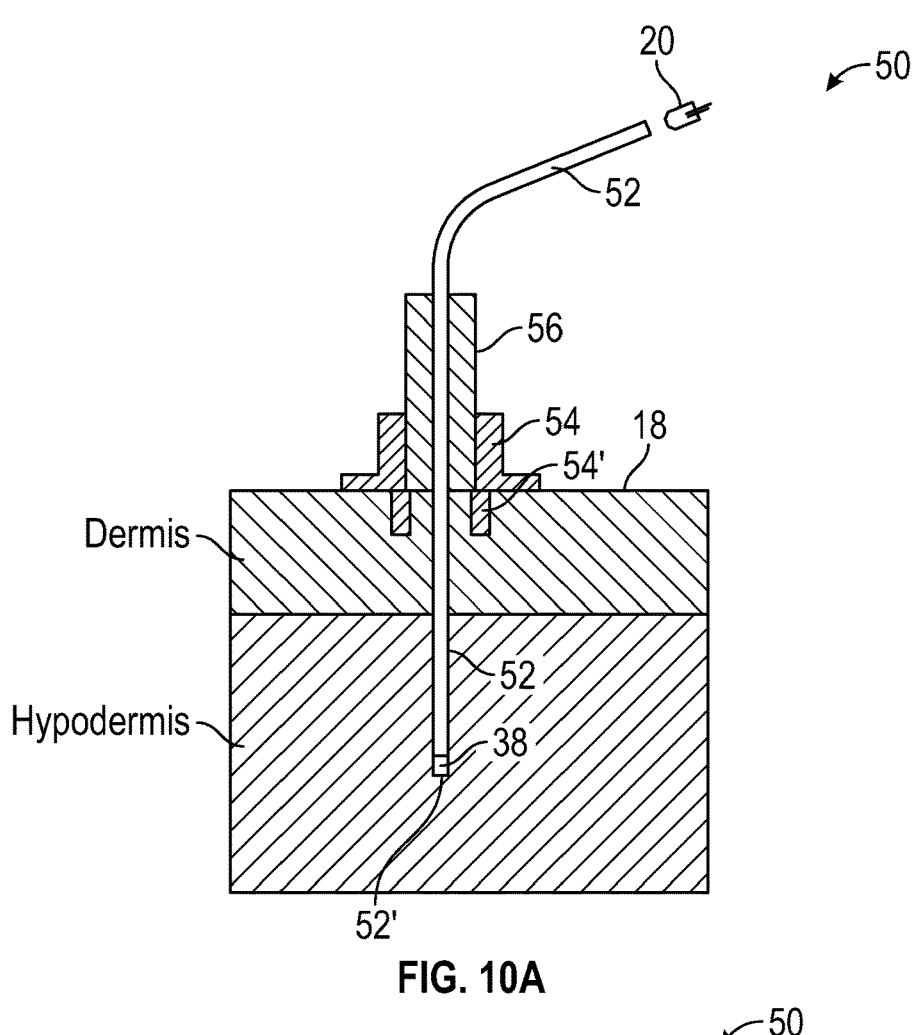
FIG. 10A is an illustration of a device with a light delivery structure and corresponding cannula support for delivering light percutaneously to provide FBR-modulating capabilities.
Figure 10B:
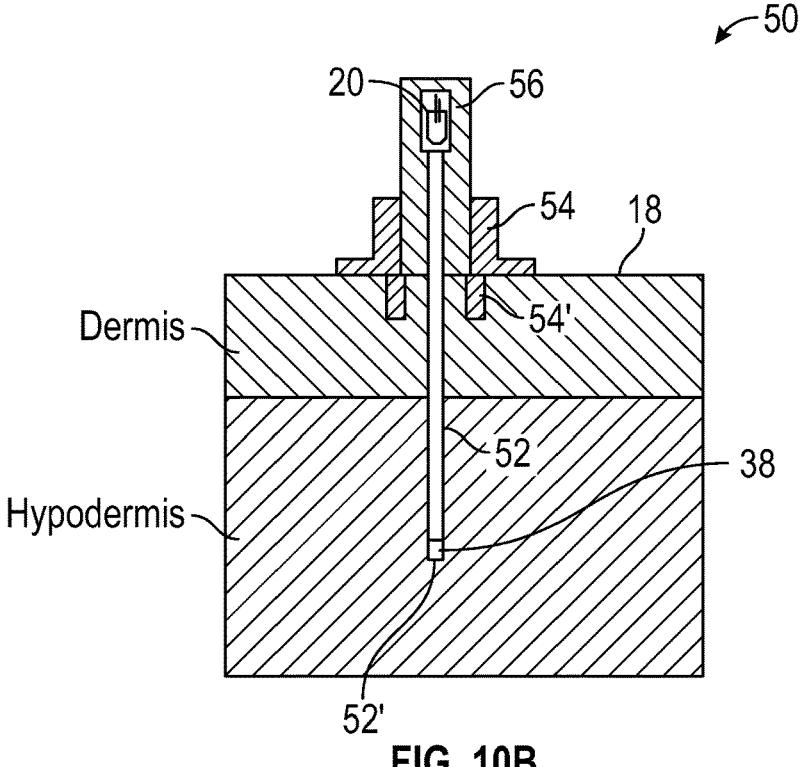
FIG. 10B is an illustration of alternative configuration of the device of FIG. 10A for embodiments where the light source may be incorporated within the housing.

FIG. 10A is an illustration of a device 50 with a light delivery structure 52 and corresponding cannula support 54 for delivering light percutaneously to provide FBR-modulating capabilities. The light delivery structure 52 may comprise an optical waveguide in the form of a fiber optic or fiber optic cannula. The cannula support 54 may include one or more protrusions 54' that are configured for insertion beneath the surface of the skin 18 and into the dermis for improved mechanical support of the light delivery structure 52. Additionally, other portions of the cannula support 54 may be secured to surfaces of the host's skin 18 by way of an adhesive. The light delivery structure 52 may include a flange or housing 56 that is sized to engage the cannula support 54 and form a stopper for the light delivery structure 52 during insertion. For example, after the cannula support 54 is secured to the host's skin 18, the light delivery structure 52 may be guided through an opening in the cannula support 54 and into the skin 18. In turn, the housing 56 may engage with a portion of the cannula support 54 to set a depth of the light delivery structure 52 beneath the skin 18. In this manner, the housing 56 and cannula support 54 may collectively provide a distal end 52' of the light delivery structure 52 at a desired depth, such as within the hypodermis as illustrated. The light source 20 may be externally arranged to provide light to the light delivery structure 52. In certain embodiments, such an arrangement may be utilized for testing and/or delivery of FBR-modulating light in a clinician's office. FIG. 10B is an illustration of an alternative configuration of the device 50 of FIG. 10A for embodiments where the light source 20 may be incorporated within the housing 56. In this regard, once the light delivery structure 52 is inserted beneath the skin 18, the housing 56 and incorporated light source 20 may allow increased mobility of the host user.

As illustrated in FIGS. 10A and 10B, the light delivery structure 52 may include the light-scattering region 38 arranged at the distal end 52' to promote light extraction. In certain embodiments, the light-scattering region 38 is provided with a small surface area compared with the remainder of the light delivery structure 52 to concentrate light that exits at the distal end 52'. By way of example, the portion of the light delivery structure 52 that is inserted beneath the skin 18 (e.g., a light guide or fiber optic) may have a length in a range from about 5 mm to about 15 mm beneath the skin 18, a diameter in a range from 8 microns ($\mu$m) to 250 $\mu$m, and a length of the light scattering-region 38 as measured from the distal end 52' may be less than the diameter. In this regard, a substantially large portion of light that may propagate within the light delivery structure 52 may exit at the distal end 52', thereby allowing high doses of delivered light relative to an amount of light provided by the light source 20. Such an arrangement may be advantageous for improving lifetimes of power sources in portable applications, where the power sources may include a battery or a rechargeable power source.

The devices illustrated in FIGS. 10A and 10B may be provided as part of CGMs or other monitoring devices to provide FBR-modulating light at or near sensor probes beneath the skin. In alternative applications, the devices illustrated in FIGS. 10A and 10B may be well suited for delivery of therapeutic doses of light to subcutaneous tissue, or the hypodermis, for purposes beyond the modulation of FBR. In this regard, the principles of the present disclosure may also be applicable to subcutaneous delivery of light even when a foreign body is not present. In other applications, devices as illustrated in FIGS. 10A and 10B may also be useful as testing structures for evaluating FBR-modulating light in experimental studies. In certain applications, protocols for evaluating FBR-modulating light may use pigs (as hosts) for human models for in vivo studies. Although rats, mice and rabbits have been used in skin studies, pig skin has been shown to be similar to human skin in many aspects, including human epidermal thickness and dermal-epidermal thickness ratios. In addition, pigs and humans have similar hair follicle and blood vessel patterns in the skin.

The principles of the present disclosure may be applicable in a variety of CGM applications for providing FBR-modulating light during monitoring. FIGS. 11-17B are illustrations showing various arrangements of CGMs or CGM components with FBR-modulating capabilities. Exemplary arrangements include one or more of light sources and light delivery structures that may be included within a CGM and/or within an accessory that may be utilized in combination with a CGM. In certain examples, such accessories may provide the ability to retrofit a conventional CGM with FBR-modulating capabilities.

Figures 11, 12, 13:
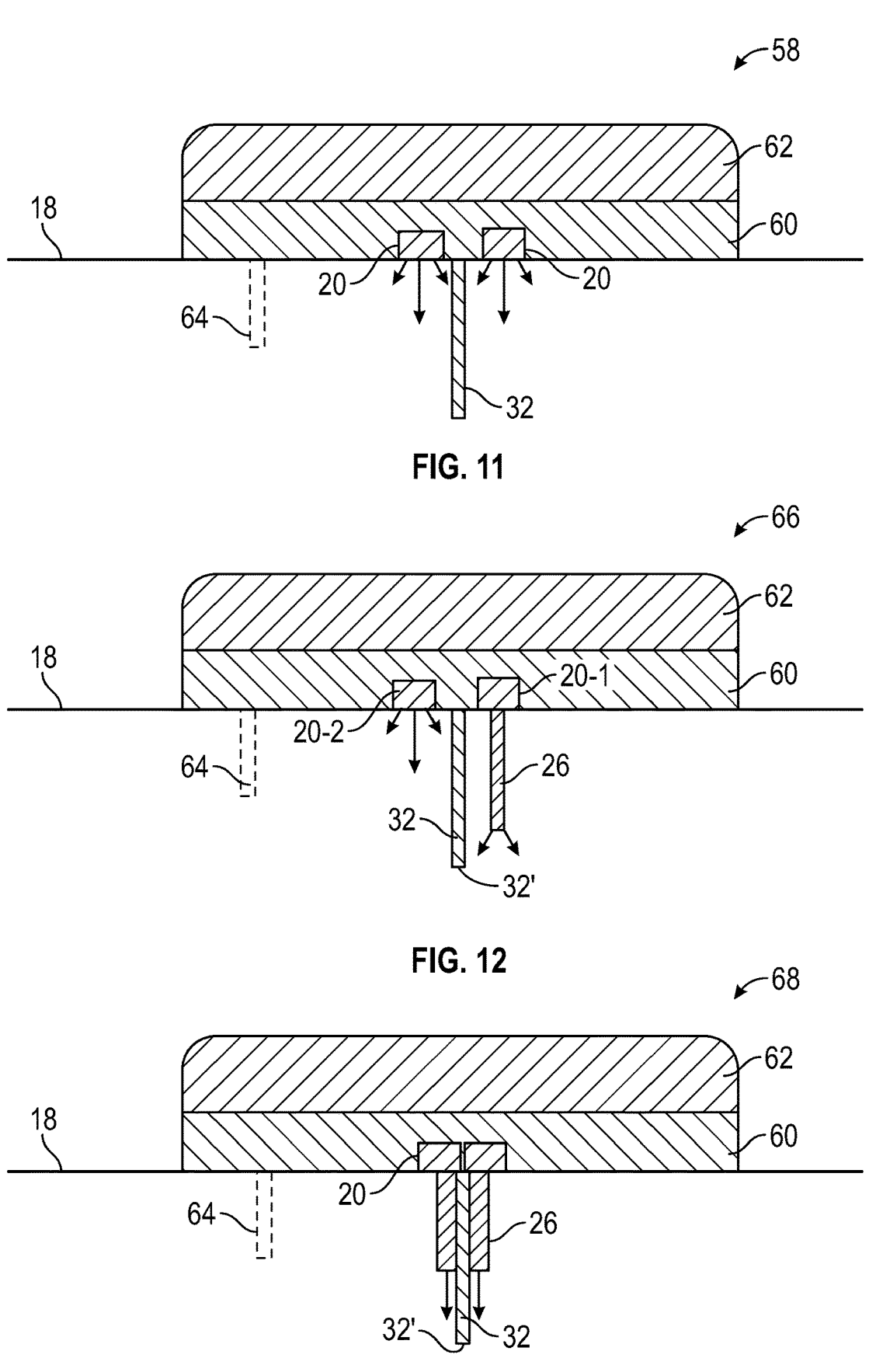
FIG. 11 is an illustration representing a CGM with an incorporated light source capable of delivering FBR-modulating light to a host's skin during monitoring.
FIG. 12 is an illustration representing a CGM that is similar to the CGM of FIG. 11 and further includes a corresponding light delivery structure capable of delivering FBR-modulating light beneath a host's skin during monitoring.
FIG. 13 is an illustration representing a CGM that is similar to the CGM of FIG. 12 and includes an alternative arrangement of the light delivery structure for delivering FBR-modulating light beneath a host's skin during monitoring.

FIG. 11 is an illustration representing a CGM 58 with an incorporated light source 20 capable of delivering FBR-modulating light to a host's skin 18 during monitoring. The CGM 58 may generally include a sensor holder 60 that includes the sensor probe 32. The sensor holder 60 may mechanically support the sensor probe 32 during percutaneous insertion. In certain configurations, the sensor probe 32 may be provided in a perpendicular manner relative to the CGM 58. However, in other configurations, the sensor probe 32 may be provided at an angle relative to the CGM 58. The sensor holder 60 is typically secured to the skin 18 by way of an adhesive as previously described. The CGM 58 may further include a transmitter 62 capable of relaying glucose sensing information to an external device, such as one or more of a portable monitor, a cell phone, a wearable device (e.g., a watch or other graphical display device), a computer, and a network. The transmitter 62 may include one or more of a power source (e.g., a battery or rechargeable battery), a microprocessor and/or microcontroller, a communications module for facilitating wireless and/or wired communications, and other associated electronics. In certain embodiments, the sensor holder 60 may be first attached to the skin 18 to position the sensor probe 32 beneath the surface of the skin 18. The transmitter 62 may thus embody a separate piece that may subsequently be attached to the sensor holder 60. In other embodiments, the sensor holder 60 and the transmitter 62 may be elements of a unitary CGM that are not removably detachable from one another. In still further embodiments, the CGM 58 may further include an optional insulin infusion catheter 64. In other embodiments, an associated insulin infusion catheter may be provided separately from the CGM 58. As illustrated in FIG. 11, one or more light sources 20 may be provided within the sensor holder 60 or the CGM 58 in an arrangement that provides light to areas of the skin 18 at or near the injection site of the sensor probe 32. Such an arrangement may be suitable for providing light to modulate the FBR at the injection site and depending on the wavelength, to depths beneath the skin 18 that correspond with tissue regions that include the sensor probe 32.

FIG. 12 is an illustration representing a CGM 66 that is similar to the CGM of FIG. 11 and further includes a corresponding light delivery structure 26 capable of delivering FBR-modulating light beneath a host's skin 18 during monitoring. In FIG. 12, the light delivery structure 26 may embody an optical waveguide, such as a fiber optic, that receives light from at least one of the light sources 20-1, 20-2 in the CGM 66. In certain embodiments, the light source 20-1 may reside within the sensor holder 60 and the light delivery structure 26 may be mechanically supported by the sensor holder 60. Accordingly, the sensor probe 32 and the light delivery structure 26 may be currently inserted beneath the skin 18. As illustrated, the light delivery structure 26 may comprise a length that is shorter than a length of the sensor probe 32 in order to deliver light at or near the distal end 32' where the active sensing region as previously described may be present. In this regard, the light delivery structure 26 may be suitable for delivering light at or near the distal end 32' in order to modulate the FBR and improve accuracy of the sensor probe 32 over time. In further embodiments, the CGM 66 may also include the light source 20-2 that is arranged to provide light to areas of the skin 18 at or near the injection site of the sensor probe 32. For example, the light source 20-1 may be configured to emit blue or near UV light that may not otherwise penetrate the skin 18 to the distal end 32' and the light source 20-2 may be configured to emit longer wavelengths, such as red and/or near IR along the surface of the skin 18.

FIG. 13 is an illustration representing a CGM 68 that is similar to the CGM of FIG. 12 and includes an alternative arrangement of the light delivery structure 26 for delivering FBR-modulating light beneath a host's skin 18 during monitoring. As illustrated, the light delivery structure 26 is arranged as a hollow structure that surrounds portions of the sensor probe 32. In this regard, the light delivery structure 26 of FIG. 13 may be similar to the light delivery structure 34 of FIG. 6 or the light delivery structure 42 of FIG. 7. For example, the light delivery structure 26 of FIG. 13 may embody sleeve, a film, a coating, or a sheath that is configured to define a light propagation pathway for delivering FBR-modulating light along portions of the sensor probe 32 and at or near the distal end 32'.

Figure 14:
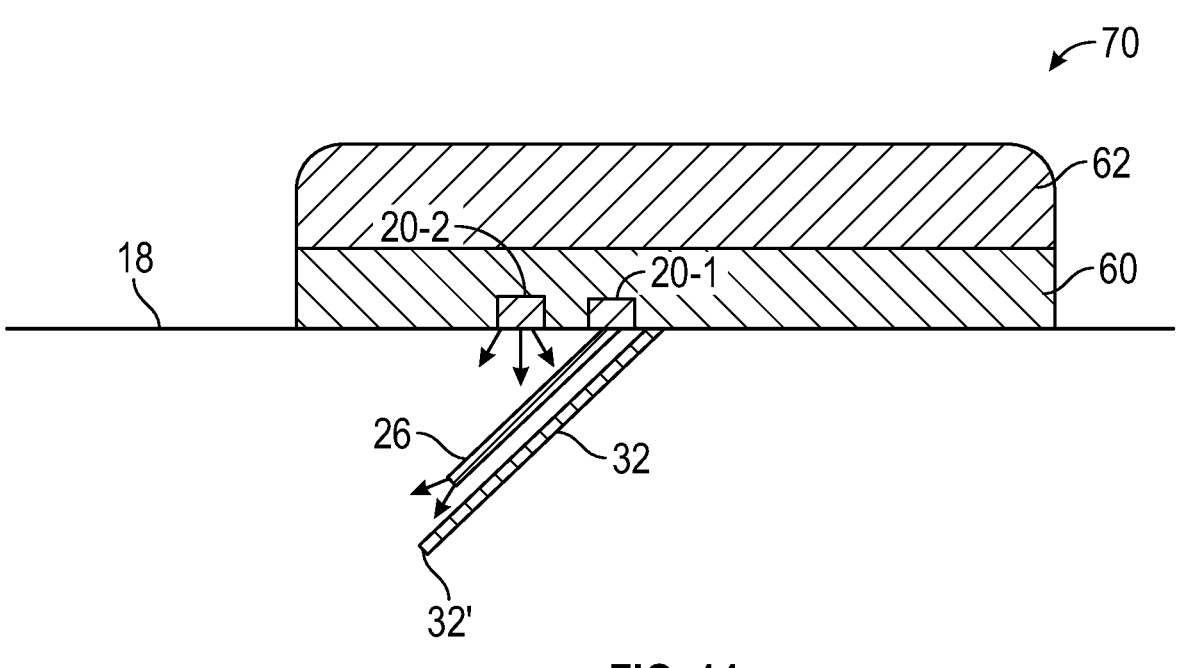
FIG. 14 is an illustration representing a CGM that is similar to the CGM of FIG. 12 and includes an angled arrangement of the light delivery structure and sensor probe for delivering FBR-modulating light beneath a host's skin during monitoring.

FIG. 14 is an illustration representing a CGM 70 that is similar to the CGM of FIG. 12 and includes an angled arrangement of the light delivery structure 26 and sensor probe 32 for delivering FBR-modulating light beneath a host's skin 18 during monitoring. Depending on the type of the CGM 70, the sensor probe 32 may be designed to reside with the host's skin 18 at an angle. As illustrated, the light delivery structure 26 may be arranged to reside within the skin 18 with a corresponding angle that is either parallel with the sensor probe 32 or within about 10 degrees of parallel from the sensor probe 32 to provide light at or near the distal end 32'. By way of example, the sensor probe 32 may be positioned with a 45 degree angle within the skin 18 and the light delivery structure 26 may be positioned with an angle in a range from 35 degrees to 55 degrees from the sensor probe 32. In certain embodiments, the light source 20-1 and corresponding light delivery structure 26 may be incorporated within the sensor holder 60. As illustrated, the CGM 70 may further include the light source 20-2 as described above for FIG. 12.

Figure 15:
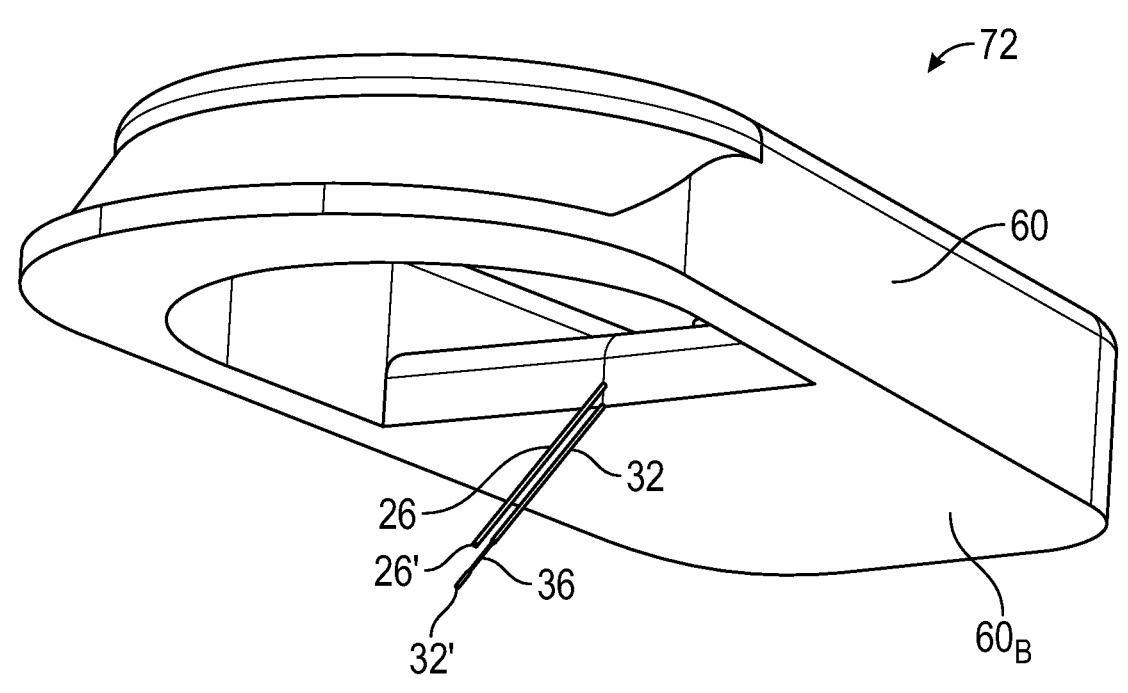
FIG. 15 is a perspective view of a portion of a CGM that may be arranged in a similar manner as the CGM of FIG. 14 for concurrent insertion of the light delivery structure with the sensor probe.

FIG. 15 is a perspective view of a portion of a CGM 72 that may be arranged in a similar manner as the CGM 70 of FIG. 14 for concurrent insertion of the light delivery structure 26 with the sensor probe 32. For illustrative purposes, the transmitter 62 is omitted in FIG. 15 to better show the sensor holder 60 and corresponding sensor probe 32 and light delivery structure 26. As illustrated, the sensor probe 32 is arranged to extend at an angle from a bottom surface 60B of the sensor holder 60. The active sensing region 36 is visible near the distal end 32' of the sensor probe 32. The light delivery structure 26 may also be incorporated with the sensor holder 60 in a position that is offset and parallel (or within 10 degrees of parallel) of the sensor holder 60. In this regard, the light delivery structure 26 may be inserted concurrently with insertion of the sensor probe 32. As illustrated, the light delivery structure 26 may be provided such that at least a portion of the light delivery structure 26, e.g., the distal end 26' in FIG. 15, may be positioned in close proximity to the active sensing region 36 of the sensor probe 32. In this regard, at least a portion of the light delivery structure 26 may be arranged to reside in a region of tissue that also includes one or more portions of the sensor probe 32. By way of example, the distal end 26' of the light delivery structure 26 may be positioned a distance of no more than 1 mm, or no more than 0.75 mm, or no more than 0.5 mm from the active sensing region 36. Such distances may be well suited for providing shorter wavelengths of light that exhibit relatively shallow penetration depths, such as less than 600 nm, or in a range from 400 nm to 600 nm, or in a range from 400 nm to 500 nm, or in a range from 400 nm to 450 nm, to the active sensing region 36. In certain embodiments, a diameter of the light delivery structure 26 may be less than a diameter of the sensor probe 32. By way of example, the diameter of the sensor probe 32 may be about 400 μm, while the diameter of the light delivery structure 26 may be in a range from 8 μm to 250 μm. In other embodiments, the light delivery structure 26 and the sensor probe 32 may have the same diameter.

Figures 16A, 16B:
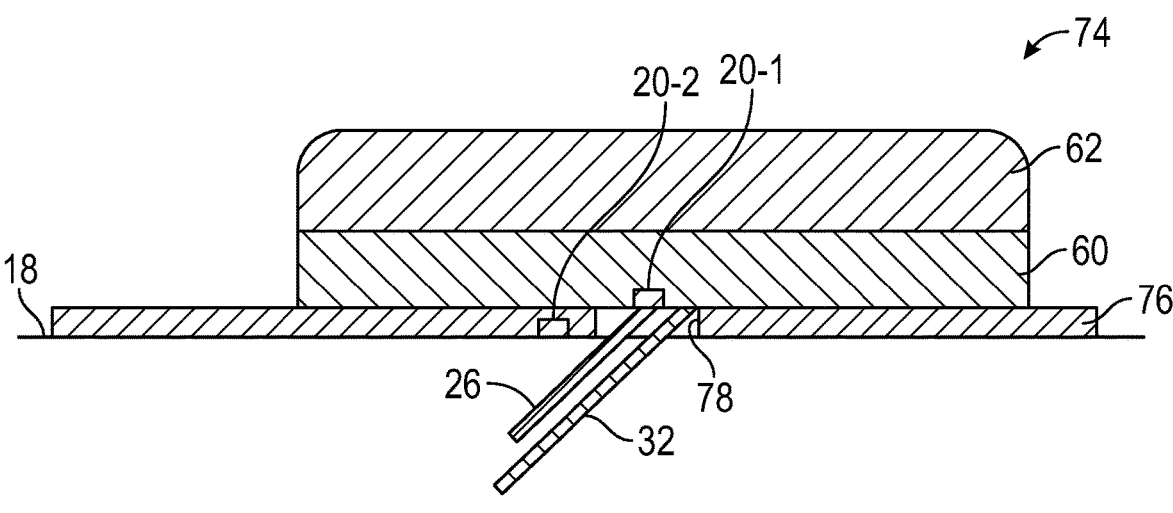
FIG. 16A is an illustration representing a CGM with a CGM accessory that is arranged between the sensor holder and the host's skin for delivering FBR-modulating light during monitoring.
FIG. 16B is an illustration representing a CGM that is similar to the CGM of FIG. 16A with an alternative configuration of the CGM accessory for delivering FBR-modulating light during monitoring.

FIG. 16A is an illustration representing a CGM 74 with a CGM accessory 76 that is arranged between the sensor holder 60 and the host's skin 18 for delivering FBR-modulating light during monitoring. In certain embodiments, the CGM accessory 76 comprises a separate structure from the CGM 74, such as a flexible printed circuit board, that includes the light source 20-2 and associated circuitry for driving the light source 20-2. As illustrated, the CGM accessory 76 may be arranged between the sensor holder 60 and the skin 18. In certain embodiments, the CGM accessory 76 may be adhesively affixed to the skin 18 or the CGM accessory 76 may embody an adhesive bandage material that is incorporated with the light source 20-2 and corresponding electronics. In certain embodiments, the CGM accessory 76 forms an opening 78 that may be registered with the sensor probe 32. In this regard, the CGM accessory 76 may first be affixed to the skin 18 and the sensor probe 32 may then pass through the opening 78 and into the skin 18 during insertion. As further illustrated, the light delivery structure 26 may also pass through the opening 78 and into the skin 18 in a concurrent manner with the sensor probe 32. Accordingly, the CGM accessory 76 may provide the ability to retrofit the CGM 74 with one or more FBR-modulating capabilities.

FIG. 16B is an illustration representing a CGM 80 that is similar to the CGM 74 of FIG. 16A with an alternative configuration of the CGM accessory 76 for delivering FBR-modulating light during monitoring. In FIG. 16B, the CGM accessory 76 includes both light sources 20-1 and 20-2. As illustrated, the light delivery structure 26 that is associated with the light source 20-1 may also be incorporated with the CGM accessory 76. In this regard, the light delivery structure 26 may first be inserted beneath the skin 18 when the CGM accessory 76 is affixed to the skin. The sensor probe 32 may then pass through the opening 78 and into the skin 18 as the sensor holder 60 is affixed to the CGM accessory 76 and/or the skin 18. In this manner, the lateral spacing of the opening 78 relative to the light delivery structure 26 may be configured to guide the sensor probe 32 into the skin 18 in a suitable position for receiving FBR-modulating light from the light delivery structure 26. While illustrated in an angled manner in FIG. 16B, both the sensor probe 32 and the light delivery structure 26 may also be arranged in a perpendicular manner without deviating from the principles disclosed.

Figure 16C:
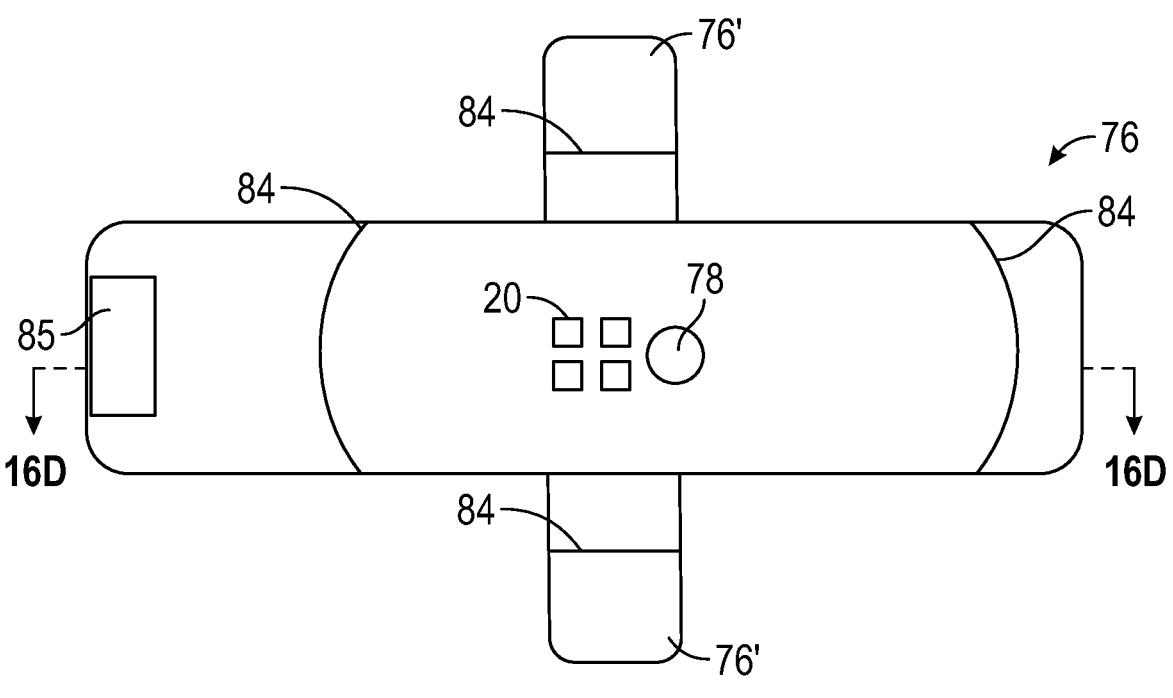
FIG. 16C is a top view of the CGM accessory of either FIG. 16A or FIG. 16B.

FIG. 16C is a top view of the CGM accessory 76 of either FIG. 16A or FIG. 16B. The CGM accessory 76 may include one or more alignment marks 84 for positioning the sensor holder 60 of FIGS. 16A and 16B relative to the opening 78 during mounting. The CGM accessory 76 may include adhesive material for adhering it to a host's skin. The CGM accessory 76 may further include optional wing portions 76' that extend past a footprint that will be occupied by the sensor holder to allow for additional forms of securing the CGM accessory 76 to the underlying skin. For example, the wing portions 76' may include their own adhesive material and/or the wing portions 76' may form tabs that can be secured with adhesive tape. In certain embodiments, the CGM accessory 76 may include a connector 85 for providing external power and/or signaling for the light sources 20. By way of example, FIG. 16C is drawn with four of the light sources 20. However, any number of the light sources 20 may be present in various configurations and combinations thereof of the light sources 20-1, 20-2 of FIGS. 16A and 16B.

Figure 16D:
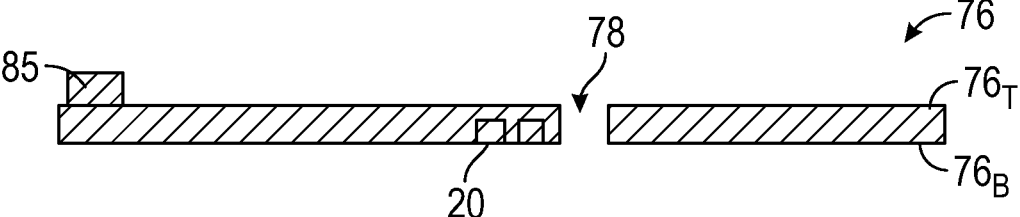
FIG. 16D is a cross-sectional view of the CGM accessory taken along the section line 16D-16D of FIG. 16C.

FIG. 16D is a cross-sectional view of the CGM accessory 76 taken along the section line 16D-16D of FIG. 16C. In certain embodiments, the CGM accessory 76 may embody a double-sided flexible member, such as a double sided flexible printed circuit board. In this manner, the connector 85 may be provided on or accessible from a top surface $76_T$ of the CGM accessory 76 and the light sources 20 may be provided on or within an opposing bottom surface $76_B$ of the CGM accessory 76. Accordingly, the connector 85 may be externally accessible while the light sources 20 may be positioned to provide FBR-modulating light to the underlying skin. In certain embodiments, one or both of the top surface $76_T$ and the bottom surface $76_B$ may include a thermally conductive coating or film, such as copper, that may serve as a thermal spreader to dissipate heat away from the light sources and toward either the surrounding air or the underlying skin.

Figure 17A:
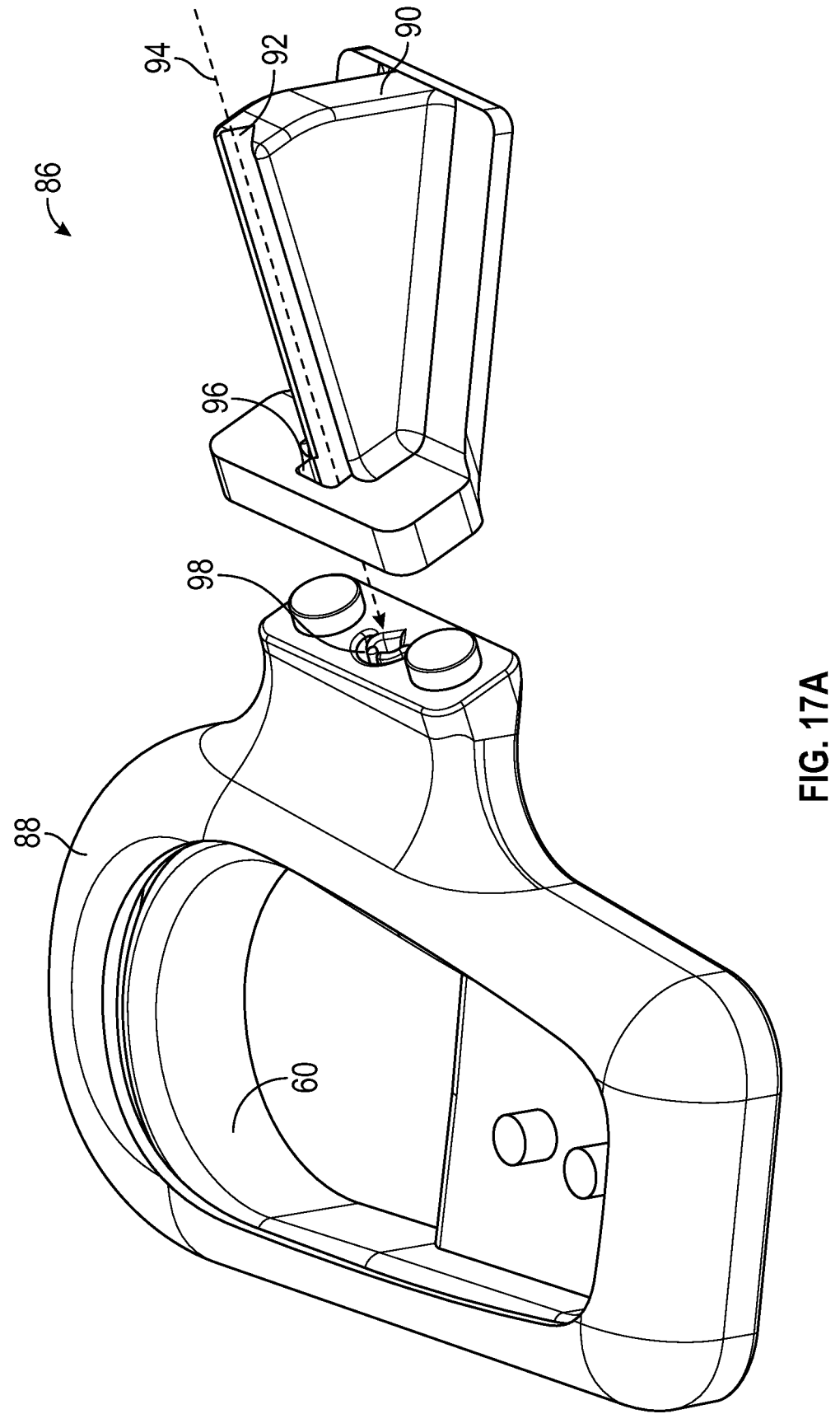
FIG. 17A is an exploded top perspective view of an assembly that provides the capability to retrofit a conventional CGM with FBR-modulating light capabilities.

FIG. 17A is an exploded top perspective view of an assembly 86 that provides the capability to retrofit a conventional CGM with FBR-modulating light capabilities. As illustrated, a light delivery structure holder 88 that is a separate structure from the CGM may be arranged along a lateral perimeter of the sensor holder 60. In certain embodiments, the light delivery structure holder 88 may be affixed to the sensor holder 60 after the sensor holder 60 is positioned on a host's skin by way of a mechanical connection. The mechanical connection may comprise a snap-fit, press-fit, spring-clip, or other suitable mechanical connection for securing the light delivery structure holder 88 in place. An insertion guide 90 may be provided that is removably attachable to a portion of the light delivery structure holder 88. The insertion guide 90 may include a channel 92 that serves as a guide for inserting a light delivery structure as previously described (e.g., 26 of FIG. 4 or 52 of FIGS.

10A-10B). An insertion path 94 that is defined by the channel 92 is illustrated with a superimposed dash-line arrow in FIG. 17A. As illustrated, the insertion path 94 extends through an opening 96 of the insertion guide 90 and through a corresponding opening 98 of the light delivery structure holder 88. In certain embodiments, a relative size of the opening 98 may form a stopper for controlling a depth of insertion for an exemplary light delivery structure along the insertion path 94. After insertion of the light delivery structure, the insertion guide 90 may be detached from the remainder of the assembly 86.

Figure 17B:
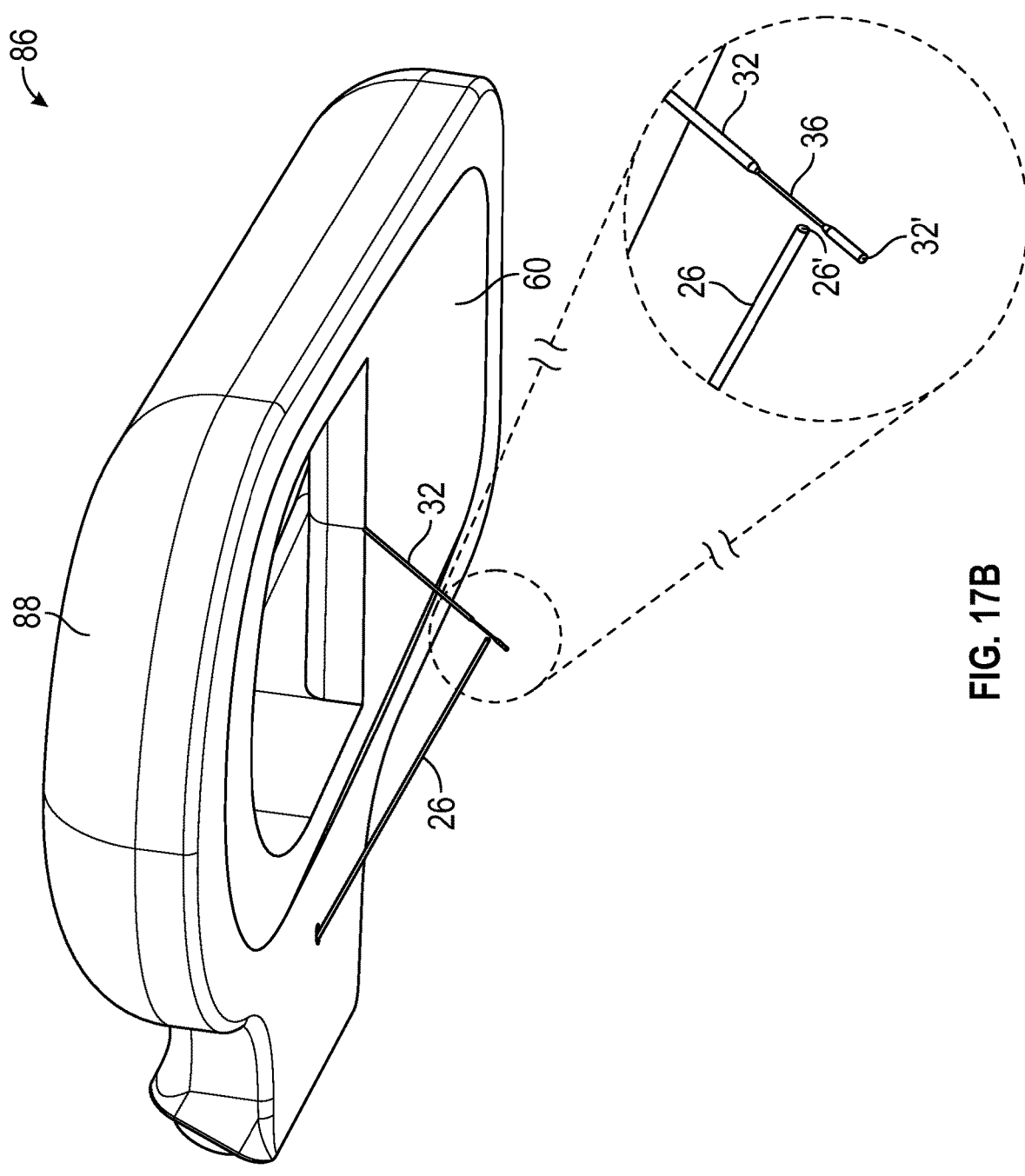
FIG. 17B is a bottom perspective view of the assembly of FIG. 17A after insertion of a light delivery structure and removal of a corresponding insertion guide.

FIG. 17B is a bottom perspective view of the assembly 86 of FIG. 17A after insertion of the light delivery structure 26 and removal of the insertion guide 90. As illustrated, the sensor probe 32 may be incorporated with the sensor holder 60. In this regard, the sensor probe 32 may first be inserted into a host's skin. The light delivery structure holder 88 may then be attached to the sensor holder 60 and the light delivery structure 26 may be inserted by way of the insertion guide 90 of FIG. 17A. As illustrated, the light delivery structure 26 may thus be provided at different angle than the sensor probe 32. In certain embodiments, such an arrangement may allow a distal end 26' of the light delivery structure 26 to be precisely positioned at or near the active sensing region 36 of the sensor probe 32. By way of example, the distal end 26' of the light delivery structure 26 may be positioned to point toward the active sensing region 36 at a distance of no more than 1 mm, or no more than 0.75 mm, or no more than 0.5 mm from the active sensing region 36.

Figure 18:
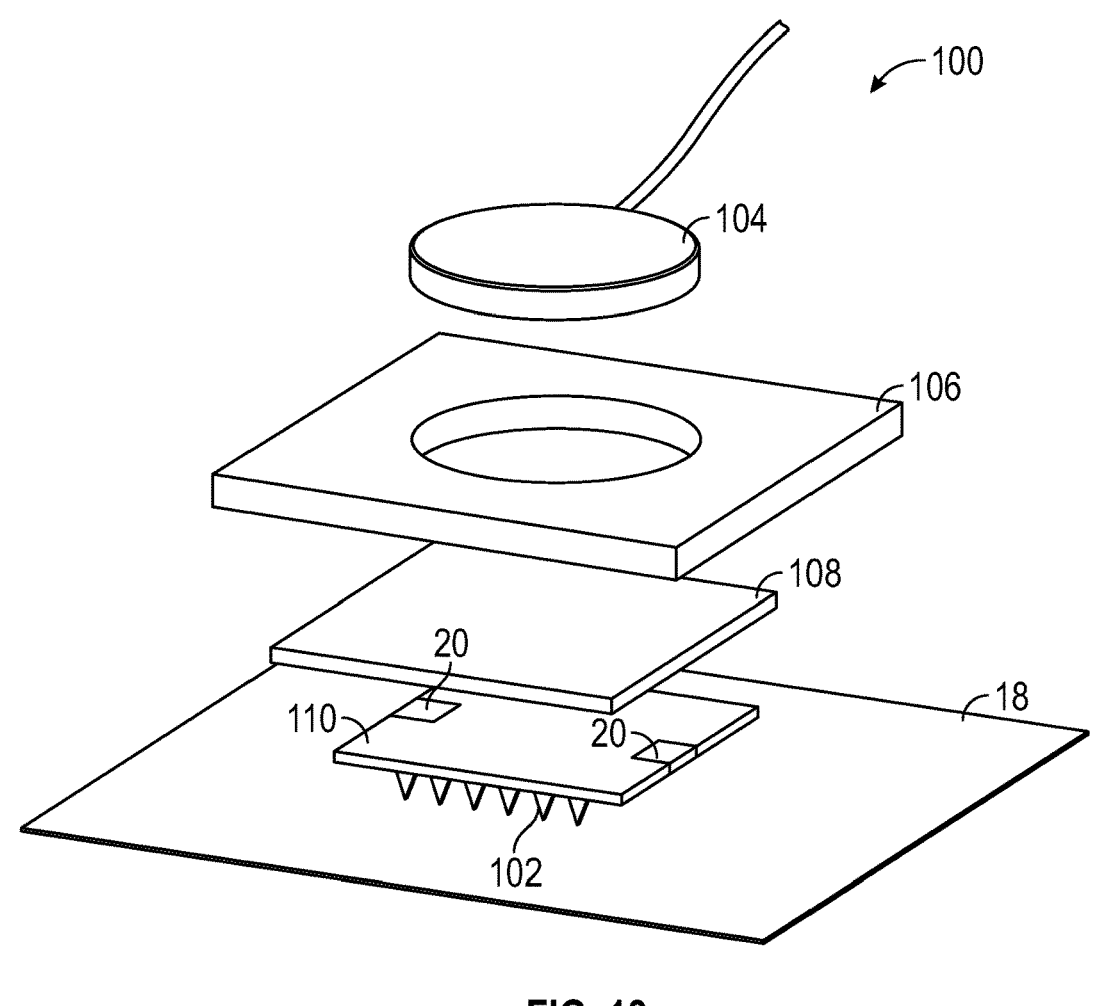
FIG. 18 is an exploded perspective view of a sensing device with a microneedle array for sensing and one or more light sources for providing FBR-modulating light capabilities.

FIG. 18 is an exploded perspective view of a sensing device 100 with a microneedle array 102 for sensing and one or more light sources 20 for providing FBR-modulating light capabilities. In certain embodiments, the sensing device 100 is a CGM with the microneedle array 102 forming probes for monitoring glucose levels within the skin 18. The sensing device 100 may include an electrode 104, such as a silver/silver-chloride electrode, that is provided in a frame 106 of silicone for example. A hydrogel material 108 may be provided between the electrode 104 and frame 106 and the microneedle array 102. The microneedle array 102 may form part of a microneedle chip 110. In certain embodiments one or more light sources 20 may be provided within the sensing device, such as incorporated with the microneedle chip 110 for providing FBR-modulating light on or near portions of the skin 18 where the microneedle array 102 is inserted.

Figure 19:
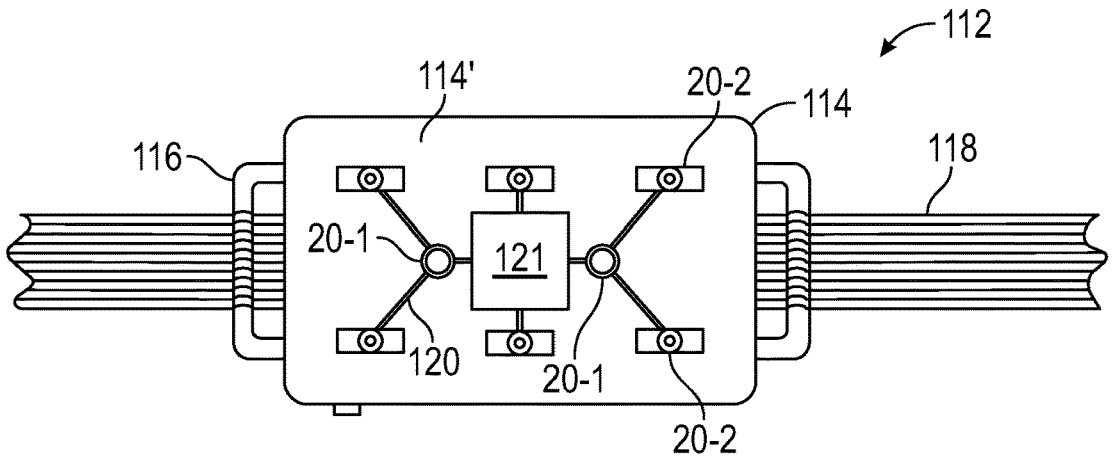
FIG. 19 is an illustration of a light-emitting bandage with FBR-modulating capabilities according to principles of the present disclosure.

FIG. 19 is an illustration of a light-emitting bandage 112 with FBR-modulating capabilities according to principles of the present disclosure. The light-emitting bandage 112 may include a body or housing 114 having attached thereto one or more strap hooks 116 for receiving a strap 118 for supporting the bandage 112. One or more types of light sources 20-1, 20-2 may be distributed about an area of a surface 114' of the housing 114 and can be interconnected by electrical connectors 120. The light sources 20-1, 20-2 may include LEDs, lasers, or other types of light sources as previously described. In certain embodiments, the one or more light sources 20-1 may be configured to emit different wavelengths of light than the one or more light sources 20-2. For example, the light sources 20-1 may be configured to emit blue or near UV light while the light sources 20-2 may be configured to emit red or near IR light. In yet another example, the one or more light sources 20-1, 20-2 may be of the same type of light source configured to emit the same or similar wavelengths of light. In still further embodiments, the light sources 20-1, 20-2 may be of different types of light sources, such as LEDs for the light sources 20-1 and lasers for the light sources 20-2. By way of a particular example, the lasers may comprise vertical-cavity surface-emitting lasers (VCSELs) emitting light at a wavelength in a range from 600-800 nm with a nominal power output of between around 2 and around 100 milliwatts. The electrical connectors 120 may include flexible, flat wire connectors or traces formed on the housing 114. In certain embodiments, the electrical connectors 120 may lead to a control module 121 that is incorporated within the housing 114. The control module 121 may also include a central power supply along with other control circuitry elements. The housing 114 may comprise a molded silicone material that is bonded to a flexible printed circuit board and when present, the power supply may include a flexible lithium polymer battery.

The light-emitting bandage 112 of FIG. 19 may be used to provide FBR-modulating light at a surface of a host's skin and/or beneath the skin to tissue surrounding an inserted biosensor. In this manner, the light-emitting bandage 112 may embody a light delivery device or devices capable of delivering light having desired FBR-modulating characteristics (e.g., wavelength characteristics, irradiance flux density, duration, pulsing or non-pulsing, coherency, etc.) as described above. The light-emitting bandage 112 may further include an incorporated biosensor in certain embodiments, while in other applications, the light-emitting bandage 112 is a structure that is separate from a conventional biosensor. For embodiments with a biosensor, the control module 121 may further include a communications module that comprises a telemetry/transmission portal for transmission of sensed information (e.g., glucose concentrations) to a display. Such display may further be incorporated in the housing or the display may be provided by an external device. The light-emitting bandage 112 may also include an adhesive layer for promoting adhesion to the underlying skin. While the term bandage is used in the context of the light-emitting bandage 112, the principles described above for FIG. 19 may also be applicable for other types of wearable light-emitting devices, such as a sleeve, cuff or a band, and light-emitting coverings, such as a blanket or a pad.

In various embodiments, the principles described above for percutaneous foreign bodies may also be applicable for providing FBR-modulating capabilities for subcutaneous or implanted devices. Such devices may include cardiac implants (such as pacemakers, implantable cardiac monitors, and implantable cardioverter defibrillators), ocular implants, cochlear implants, artificial joints (such as knees, hips, shoulders, and elbows), cosmetic implants (such as breast implants, calf implants, and buttocks implants), drug delivery devices, contraceptive implants, and vascular stents. Implantable devices serve a variety of functions in the medical field, from vascular stents that preserve blood flow to electrostimulation devices that regulate heart rhythm or block spurious signals in the brain, to orthopedic devices that mechanically reinforce the spine or restore range of motion of hips, shoulders, elbows, and knees. Implantable devices also are used as controlled drug delivery systems. By applying principles of the present disclosure to implantable devices, FBR may be modulated with light to reduce infections and/or mitigate the impact of collagen matrix formation on device functions. Embodiments for implantable devices as disclosed herein may include an energy storage device and various electronics for powering and controlling operation of one or more associated light sources.

Cardiac implants may include, for example, pacemakers, implantable cardioverter defibrillators, and implantable cardioverter defibrillators. Long-term performance of cardiac implants over years of operation may be decreased by FBR, and infections during implantation can pose increased costs, as well as increased risk of mortality and morbidity. In this regard, aspects of the present disclosure provide cardiac implant devices that include light-based FBR modulating capabilities.

FIG. 20A schematically depicts a pacemaker 122 that may include light-based FBR modulating capabilities according to the present disclosure. The pacemaker 122 may comprises a pulse generator 124 and pulsing leads 126 positioned to deliver electrical pulses from the pulse generator 124 to various positions 126a-c of a patient's heart 128. The pulse generator 124 typically comprises a housing 130 with a heart sensor 132 that is positioned within the housing 130. The pacemaker 122 is typically a small device that is placed under the skin in the chest to help control a user's heartbeat. It is commonly used for patients with an irregular heartbeat (arrhythmia), particularly a slow one. The pacemaker 122 may be surgically implanted in the user's chest. Example embodiments of the pacemaker 122 include a single chamber pacemaker that carries electrical impulses to the right ventricle of the heart 128, a dual chamber pacemaker that carries electrical impulses to the right ventricle and the right atrium of the heart 128 to help control the timing of contractions between the two chambers, and a biventricular pacemaker that stimulates the lower chambers of the heart 128 (i.e., the right and left ventricles) to make the heart 128 beat more efficiently. During use, fibrous capsules associated with FBR may enclose one or more portions of the pulsing leads 126 and increase the excitation threshold, thereby requiring more energy from the energy storage device, or even preventing the treatment from reaching the target tissue altogether. Accordingly, the prevention, minimization, and/or modulation of the FBR may extend the pacemaker's 122 useful life and/or reduce complications associated with initial infection and/or inflammation. In this regard, the housing 130 may further include one or more light sources 134 that may be optically coupled to deliver light along one or more of the pulsing leads 126 and the exterior of the housing 130. For example, the pulsing leads 126 may be at least partially encased with a light guide material for propagating FBR-modulating light from the light source 134 along portions of the pulsing leads 126. Additionally, the housing 130 may be encased with a light guide material to deliver FBR-modulating light to the exterior of the housing 130. As with other embodiments, the light source 134 may provide multiple wavelength capabilities that provide longer wavelengths, such as red and/or near IR to promote healing and reduce rejection during early stages of the FBR sequence and shorter wavelengths, such as blue and/or near UV, to mitigate formation of fibrous tissue that may otherwise encapsulate portions of the pacemaker 122. The light source 134 may be electrically driven with a same power source for the remainder of the pacemaker 122 or the light source 134 may include a separate power source within the housing 130.

FIG. 20B is a schematic view of a portion the housing 130 of FIG. 20A, illustrating an arrangement of the light source 134. As illustrated, the light source 134 (e.g., an LED) may be provided on a support structure 136 of the housing 130. A light delivery structure 138, such as a light guide material layer or coating, may provide an encapsulation layer along an exterior of the housing 130. As illustrated, the light source 134 may emit light into the light delivery structure 138 where it may propagate along exterior surfaces of the housing 130 to modulate FBR. In certain embodiments, the light delivery structure 138 may contain a wavelength conversion material for converting a least a portion of light from the light source 134 to a different wavelength.

FIG. 20C is a schematic view of a portion of a surface of the housing 130 of FIG. 20A, illustrating another arrangement of the light source 134. In certain embodiments, the light source 134 may be positioned in a recess in a surface 130' of the housing 130, and a light delivery structure 140 (e.g., a light pipe, a fiber, a diffuser, one or more lenses, a digital light processor, an index matching feature, etc.) may be positioned where light emitted from the light source 134 may enter the light delivery structure 140 for delivery of FBR-modulating light to other portions of the pacemaker 122, such as along the pulsing leads 126. The light delivery structure 140 of FIG. 20C may be used in combination with the light delivery structure 138 of FIG. 20B. In certain embodiments, the light delivery structure 140 may comprise a similar structure as previously described for the light delivery structures 26, 34, 42, and 46 of previous figures.

FIG. 21 is a schematic view 142 of an implantable cardioverter defibrillator (ICD) 144 implanted in a patient 146, where the ICD 144 includes FBR-modulating capabilities according to the present disclosure. The ICD 144 may comprise a housing 148 and an electrode 150. The ICD 144 may comprise a light source 152 that is similar to the light source 134 of FIGS. 20A-20C. The light source 152 may be arranged on or within the housing 148. Alternatively, the light source 152 may be positioned at the electrode 150, or at both the housing 148 and the electrode 150. The light source 152 may be arranged with one or more of the light delivery structures 138, 140 as illustrated in FIGS. 20B or 20C. The ICD 144 is typically a small (usually battery-powered device) placed in a patient's chest to monitor heart rhythm and detect irregular heartbeats (arrhythmias). The ICD 144 can deliver electric pulses or shocks via one or more wires connected to the user's heart to mitigate an abnormal heart rhythm. Patients use ICDs to control dangerously fast heartbeats (ventricular tachycardia) or chaotic heartbeats that keep the heart from supplying enough blood to the rest of the body (ventricular fibrillation). The ICD 144 is surgically placed under the skin of the patient 146, usually below the left collarbone and one or more flexible, insulated wires (leads) may run from the ICD 144 through the veins to the heart. The ICD 144 constantly monitors for abnormal heart rhythms and instantly tries to correct them. This is particularly useful when a heart stops beating in cardiac arrest. The ICD 144 sends electrical pulses to regulate heartbeat. ICDs can be programmed for low-energy pacing to address mild disruptions in heartbeat, and higher-energy shocks for more serious heart rhythm problems. Mechanical tissue damage during the surgical insertion (acute trauma), as well as long term contact of microelectrodes with electrically excitable tissues and micro movements associated with electrode anchoring (chronic disturbance) induce activation of cells implicated in a FBR. Accordingly, it is advantageous to modulate FBR by way of the light source 152 using the techniques described herein. The light source 152 may be electrically driven with a same power source for the remainder of the ICD 144 or the light source 152 may include a separate power source within the housing 148.

FIG. 22 is a schematic view 154 of an implantable cardiac monitor (ICM) 156 implanted in a patient 158, where the ICM 156 includes FBR-modulating capabilities according to the present disclosure. The ICM 156 may comprise a light source 160 that is similar to the light source 134 of FIGS.

20A-20C. The light source 160 may be electrically driven with a same power source for the remainder of the ICM 156 or the light source 160 may include a separate power source within the ICM 156. ICMs are typically small electrophysiology (EP) devices used for long-term monitoring of a patient's heart electrical activity to detect arrhythmias. ICMs may eliminate the need for bulky external Holter monitors that use wire leads attached to the patient. The ICM 156 may be inserted under the skin of the patient 158 to continuously monitor the patient's electrocardiogram and perform real-time analysis of the heart rhythm over an extended time period, such as up to 36 months. However, typical ICMs may eventually fail, and in many cases their failure may be attributed to, at least in part, the body's innate FBR. By including the light source 160 and various corresponding light delivery structures according to the present disclosure, FBR-modulating light may extend operating lifetimes of ICMs.

FIG. 23 is a schematic view of a cochlear implant 162 within a patient 164, where the cochlear implant 162 includes FBR-modulating capabilities according to the present disclosure. The cochlear implant 162 may comprise an electrode array 166 arranged along the cochlea, a receiver/stimulator 168, a transmitter 170, a speech processor 172 and a microphone 174. The cochlear implant 162 may further comprise a light source 176 that is similar to the light source 134 of FIGS. 20A-20C. The cochlear implant 162 is typically a small electronic device that electrically stimulates the cochlear nerve for hearing. Persons of skill in the art are familiar with a wide variety of cochlear implants, and the devices and methods according to the present invention can employ any of such cochlear implants. The cochlear implant 162 may have external parts including the microphone 174 for receiving sound. In response, the cochlear implant 162 processes the sound and transmits it to the internal parts via an implanted wire 177 to the implanted electrode array 166. An active FBR to implanted portions of the cochlear implant 162 (e.g., the wire 177 and electrode array 166) may be anticipated to result in device degradation and/or failure. The severity of the FBR may be negatively correlated with performance and with the preservation of acoustic hearing following implantation. Since the cochlear implant 162 is intended to be a long-term implant, even a slowly progressing FBR can result in performance degradation or other problems. Accordingly, it is advantageous to minimize or prevent the onset of FBR using the techniques described herein. In certain embodiments, the light source 176 may be incorporated in one of more of the external parts, such as the receiver/stimulator 168 and a light delivery structure, such as a fiber-optic light with an optional diffuser at the end may be provided to propagate light along implanted portions to modulate FBR. In certain embodiments, an energy storage device of the cochlear implant 162 may be utilized to also provide power to the light source 176. Since replacement of cochlear implants involves inherent risks, it is advantageous to improve their long-term functionality by modulating FBR.

The principles of the present disclosure may also be applicable for providing FBR-modulating light for total and/or partial joint replacement implants, as well as cosmetic implants, drug delivery systems, and intrauterine devices. Total joint replacement (TJR) and partial joint replacement may be used to treat end-stage arthritis that can otherwise be disabling. Persons of skill in the art are familiar with a wide variety of artificial joints, and the devices and methods according to the present invention can employ any of such artificial joints. TJRs may be utilized in large joints such as the hip, knee, shoulder, and/or elbow. Different bearing surfaces can be used, but the most common are metal-on-polyethylene (MOP), ceramic-on-ceramic (COC), or metal-on-metal (MOM). Biomaterials used must be resistant enough to support weight bearing of the joint, while also minimizing adverse effects on the surrounding tissues and avoiding infection. While most modern materials are well-tolerated as long as they remain in bulk form, achieve mechanical stability within bone, and are not colonized by microorganisms to produce chronic infection, excessive wear can generate wear particles or ionic complexes. This can result in acute and chronic inflammation, which may induce periprosthetic osteolysis, loss of bony support subsequent loosening, and implant failure. Additionally, an initial local inflammatory response post-surgery can lead to further complications. Accordingly, while orthopedic implants used for joint replacement are effective in relieving pain and restoring function, they have a limited life expectancy due to wear and possible foreign body response to wear byproducts (including particles). In this regard, aspects of the present disclosure may be applicable to various joint replacement structures that are implanted in the hip, knee, shoulder, and/or elbow as well as other implantable devices that may elicit an FBR, such as cosmetic implants, drug delivery systems, and intrauterine devices. Such structures may include light sources and corresponding power supplies that are integrated within joint replacement structures.

FIG. 24 is a schematic view of an artificial knee 178 that includes FBR-modulating capabilities according to the present disclosure. The artificial knee 178 may comprises a first prosthesis 180 (attached to the femur) and a second prosthesis 182 (attached to the tibia). The artificial knee 178, including one or more of the first prosthesis 180 and the second prosthesis 182, may further comprise one or more light sources 184 that are similar to the light source 134 of FIGS. 20A-20C for providing FBR-modulating light. While FIG. 24 is provided in the context of an artificial knee, the principles disclosed may also be applicable to other implants, including cosmetic implants, drug delivery systems, and intrauterine devices that include one or more FBR-modulating light sources in a similar manner.

According to principles of the present disclosure, one or more light sources may be provided to modulate an FBR associated with percutaneous and/or subcutaneous devices. The one or more FBR-modulating light sources may be incorporated as either a separate structure from the device or a structure that is integrated with the device. Power sources and/or control circuitry for electrically activating and controlling such light sources may be integrated with existing power sources and control circuitry of the devices. In other embodiments, the power sources and/or control circuitry for electrically activating and controlling the light sources may be separate from those that power and control other functions of the device. In still further embodiments where the device does not otherwise require a power source and/or control circuitry (e.g., a joint replacement, cosmetic implant, etc.), various elements of the electronics may be incorporated integrally and/or remotely to operate the light sources. In certain embodiments, power supplies for implants may include rechargeable batteries that may be recharged inductively, optically with a photovoltaic cell, ultrasonically, and/or electromagnetically. Additional power sources of FBR-modulating light sources of implantable devices may include energy that is generated and harvested from potential sources surrounding the implants, for example, using biofuel cells that exploit glucose and oxygen, which are abundant in the blood to generate energy. Power may also be harvested from body heat and or body movements, such as breathing and motion, by way of thermoelectric generators and/or piezoelectric generators.

FIG. 25 is a schematic diagram of a control scheme for a device 186 that includes FBR-modulating capabilities according to the present disclosure. The device 186 may represent a percutaneous device such as a CGM or other biosensor, a subcutaneous device that is fully implanted beneath a host's skin, or a topical device such as a bandage, blanket or other covering. As illustrated, the device 186 may include a power source 188 and a control module 190 that are configured to provide power and controls to both a medical device 192 and a light source 194. The power source 188 may include a battery and/or a rechargeable battery, among the other integrated power supplies. The control module 190 may include active electronics, such as a microprocessor and/or microcontroller, that actively control and/or determine dosing parameters such as duration, interval, and wavelength provided by the light source 194 as well providing power and other operating functions to the medical device 192. In other embodiments, the control module 190 may embody passive electronics that only deliver power to the light source 194. In such embodiments, dosing parameters may be controlled by external electronics, including those that operate by radio-frequency communication. By way of example, the device 186 may embody a CGM and the medical device 192 may accordingly represent the sensor probe for glucose monitoring. For such embodiments, the same control module 190 and power source 188 used to operate the glucose monitoring functions of the device 186 may also be used to operate the light source 194. By way of another example, the device 186 may embody a pacemaker where the medical device 192 represents a heart sensor and pulsing leads. Accordingly, the same control module 190 and power source 188 that operate the sensing and pacing functions of the pacemaker may also be used to operate the light source 194. In yet another example where the device 186 represents a structure that does not otherwise require integrated power sources and control modules, such as an orthopedic implant, a catheter, and/or a chemotherapy port, the power source 188 and the control module 190 may be incorporated exclusively to control operation of the light source 194.

FIG. 26 is a schematic diagram of a control scheme for a device 196 that is similar to the device 186 of FIG. 25, except that operation of the light source 194 is provided separately from other functions of the device 196. In this regard, the medical device 192 may be powered and controlled by a first power source 188-1 and a first control module 190-1 while the light source 194 is powered and controlled by a second power source 188-2 and a second control module 190-2. In this regard, FBR-modulating light may be delivered by dedicated electronics that are separate from other functions of the device 196.

FIG. 27 is a schematic diagram of a control scheme for a device 198 that is similar to the device 186 of FIG. 25, except that at least a portion of the power source 188 is provided remotely from the device 198. In this regard, the power source 188 may embody an inductively coupled power supply for providing wireless power transmission to the control module 190, medical device 192, and light source 194. Such a configuration may be useful for applications where the device 198 may not be easily accessible, such as one or more of the subcutaneous devices previously described.

FIG. 28 is a schematic diagram of a control scheme for a device 200 that is similar to the device 196 of FIG. 26, except that operation of the light source 194 is provided separately from other functions of the device 200. In this regard, the first power source 188-1 and first control module 190-1 may be incorporated within the device 200 to control functions related to the medical device 192 while the second power source 188-2 is provided remotely as described for FIG. 27. In such embodiments, the second control module 190-2 that controls dosing parameters for the light source 194 may be incorporated within the device 200.

It is contemplated that any of the foregoing aspects, and/or various separate aspects and features as described herein, may be combined for additional advantage. Any of the various embodiments as disclosed herein may be combined with one or more other disclosed embodiments unless indicated to the contrary herein.

Those skilled in the art will recognize improvements and modifications to the preferred embodiments of the present disclosure. All such improvements and modifications are considered within the scope of the concepts disclosed herein and the claims that follow.

What is claimed is:

1. A method of modulating a foreign body response, the method comprising:
   providing a foreign body within a region of subcutaneous tissue of a host, the foreign body comprising a sensor probe having an active sensing region proximate a distal end of the sensor probe;
   providing a light source capable of emitting one or more peak wavelengths of light, the one or more peak wavelengths comprising a first wavelength in a range from 400 nanometers (nm) to 450 nm;
   inserting a light delivery structure through skin of the host such that a distal end of the light delivery structure is separated from the active sensing region by a portion of the region of subcutaneous tissue and the distal end comprises a light-scattering region integral to the light delivery structure, wherein the light-scattering region is positioned at an offset depth above the active sensing region and the light delivery structure is optically coupled with the light source; and
   irradiating one or more portions of the region of subcutaneous tissue with the light through the light-scattering region of the light delivery structure to modulate a foreign body response within the region of subcutaneous tissue.

2. The method of claim 1, wherein the light is irradiated to the one or more portions of the region of subcutaneous tissue at a tissue depth in a range from 1 millimeter (mm) to 15 mm.

3. The method of claim 1, wherein the light is irradiated to the one or more portions of the region of subcutaneous tissue at a tissue depth in a range from 4 millimeters (mm) to 15 mm.

4. The method of claim 1, wherein the one or more peak wavelengths of light comprises a second wavelength in a range from 315 nm to 400 nm.

5. The method of claim 1, wherein the one or more peak wavelengths of light comprises a second wavelength in a range from 400 nm to 1600 nm.

6. The method of claim 1, wherein the one or more peak wavelengths of light comprises a second wavelength in a range from 600 nm to 1600 nm.

7. The method of claim 6, wherein the second wavelength is in a range from 630 nm to 670 nm.

8. The method of claim 6, wherein the first wavelength is irradiated to the region of subcutaneous tissue during a first time interval and the second wavelength is irradiated to the region of subcutaneous tissue during a second time interval that is different than the first time interval.

9. The method of claim 8, wherein the first time interval overlaps with the second time interval.

10. The method of claim 8, wherein the first time interval is nonoverlapping with the second time interval.

11. The method of claim 8, wherein the first time interval is in a range from 3 to 30 days, and the second time interval is in a range from 0 days to 4 days.

12. The method of claim 8, wherein the second time interval is provided during hemostasis and inflammation stages of the foreign body response and the first time interval is provided during proliferation and remodeling stages of the foreign body response.

13. The method of claim 1, wherein inserting the light delivery structure through the skin of the host comprises positioning the distal end of the light delivery structure to be separated from the active sensing region by 1 millimeter (mm) or less of the region of subcutaneous tissue.

14. The method of claim 13, wherein the light delivery structure comprises an optical waveguide.

15. The method of claim 13, wherein the light delivery structure comprises a fiber optic with a diameter in a range from 8 microns (μm) to 250 μm.

16. The method of claim 1, further comprising irradiating skin that is above the region of subcutaneous tissue with additional light.

17. A device comprising:
a foreign body that is configured to be at least partially inserted within a region of subcutaneous tissue of a host, the foreign body comprising a sensor probe having an active sensing region proximate a distal end of the sensor probe;
a light source capable of emitting one or more peak wavelengths of light for irradiating one or more portions of the region of subcutaneous tissue to modulate a foreign body response within the region of subcutaneous tissue, the one or more peak wavelengths comprising a first wavelength in a range from 400 nanometers (nm) to 450 nm; and
a light delivery structure optically coupled with the light source, the light delivery structure configured to be inserted through skin of the host such that a distal end of the light delivery structure is separated from the active sensing region by a portion of the region of subcutaneous tissue and the distal end comprises a light-scattering region integral to the light delivery structure, and the light-scattering region is positioned at an offset depth above the active sensing region.

18. The device of claim 17, wherein the light source is provided outside the region of subcutaneous tissue for irradiating the light through a portion of the host's skin that is registered with the region of subcutaneous tissue.

19. The device of claim 17, wherein at least a portion of the light delivery structure is capable of residing within the region of subcutaneous tissue to irradiate one or more portions of the region of subcutaneous tissue.

20. The device of claim 19, further comprising an additional light source that is provided for irradiating light through a portion of the host's skin that is registered with the region of subcutaneous tissue.

21. The device of claim 17, wherein the one or more peak wavelengths of light comprises a second wavelength in a range from 315 nm to 400 nm.

22. The device of claim 17, wherein the one or more peak wavelengths of light comprises a second wavelength in a range from 400 nm to 1600 nm.

23. The device of claim 17, wherein the one or more peak wavelengths of light comprises a second wavelength in a range from 600 nm to 1600 nm.

24. The device of claim 23, wherein the second wavelength is in a range from 630 nm to 670 nm.

25. The device of claim 17, wherein the device comprises a continuous glucose monitor.

26. The device of claim 25, wherein at least a portion of the light delivery structure is capable of residing within the region of subcutaneous tissue to irradiate one or more portions of the region of subcutaneous tissue such that the distal end of the light delivery structure is separated from the active sensing region by 1 millimeter (mm) or less of the region of subcutaneous tissue.

* * * * *